(12) United States Patent
Wildman

(10) Patent No.: US 7,119,688 B2
(45) Date of Patent: Oct. 10, 2006

(54) WASTE SEGREGATION COMPLIANCE SYSTEM

(75) Inventor: Timothy D. Wildman, Metamora, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 259 days.

(21) Appl. No.: 10/884,936

(22) Filed: Jul. 6, 2004

(65) Prior Publication Data

US 2004/0250004 A1 Dec. 9, 2004

Related U.S. Application Data

(63) Continuation of application No. 10/154,644, filed on May 24, 2002, now Pat. No. 6,759,959.

(60) Provisional application No. 60/293,924, filed on May 25, 2001.

(51) Int. Cl.
*G08B 13/14* (2006.01)

(52) U.S. Cl. ............... 340/572.1; 340/572.8; 340/3.1

(58) Field of Classification Search ............. 340/572.1, 340/572.4, 572.8, 573.1, 613, 3.1, 286.07; 235/375, 376; 241/179
See application file for complete search history.

(56) References Cited

U.S. PATENT DOCUMENTS

| | | |
|---|---|---|
| 3,439,320 A | 4/1969 | Ward |
| 3,739,329 A | 6/1973 | Lester |
| 4,151,407 A | 4/1979 | McBride et al. |
| 4,216,462 A | 8/1980 | McGrath et al. |
| 4,225,953 A | 9/1980 | Simon et al. |
| 4,275,385 A | 6/1981 | White |
| 4,601,064 A | 7/1986 | Shipley |
| 4,646,385 A | 3/1987 | Roberts et al. |
| 4,728,928 A | 3/1988 | Shipley |
| 4,837,568 A | 6/1989 | Snaper |
| 4,967,195 A | 10/1990 | Shipley |
| 4,979,217 A | 12/1990 | Shipley |
| 4,990,892 A | 2/1991 | Guest et al. |
| 5,016,172 A | 5/1991 | Dessertine |
| 5,027,314 A | 6/1991 | Linwood et al. |
| 5,051,741 A | 9/1991 | Wesby |
| 5,062,151 A | 10/1991 | Shipley |
| 5,119,104 A | 6/1992 | Heller |
| 5,153,584 A | 10/1992 | Engira |
| 5,199,118 A | 4/1993 | Cole et al. |
| 5,202,666 A | 4/1993 | Knippscheer |
| 5,214,421 A | 5/1993 | Vernon et al. |
| 5,218,344 A | 6/1993 | Ricketts |
| 5,291,399 A | 3/1994 | Chaco |
| 5,317,309 A | 5/1994 | Vercellotti et al. |
| 5,319,363 A | 6/1994 | Welch et al. |

(Continued)

FOREIGN PATENT DOCUMENTS

DE 29905840 U1 3/1999

(Continued)

OTHER PUBLICATIONS

R-140, RFID, Smart Label Printer and Encoder, © 2000 Zebra Technologies Corporation.

(Continued)

*Primary Examiner*—Toan N. Pham
(74) *Attorney, Agent, or Firm*—Bose McKinney & Evans LLP

(57) ABSTRACT

A waste segregation compliance system and method including a processor, a waste receptacle configured to detect a deposit of an item therein and to provide a deposit signal to the processor, and a detector configured to detect a person and to provide a location signal to the processor in response to detection of the person.

20 Claims, 30 Drawing Sheets

U.S. PATENT DOCUMENTS

| | | |
|---|---|---|
| 5,341,412 A | 8/1994 | Ramot et al. |
| 5,363,425 A | 11/1994 | Mufti et al. |
| 5,387,993 A | 2/1995 | Heller et al. |
| 5,390,238 A | 2/1995 | Kirk et al. |
| 5,396,224 A | 3/1995 | Dukes et al. |
| 5,402,469 A | 3/1995 | Hopper et al. |
| 5,412,715 A | 5/1995 | Volpe |
| 5,417,222 A | 5/1995 | Dempsey et al. |
| 5,426,425 A | 6/1995 | Conrad et al. |
| RE35,035 E | 9/1995 | Shipley |
| 5,455,851 A | 10/1995 | Chaco et al. |
| 5,458,123 A | 10/1995 | Unger |
| 5,461,665 A | 10/1995 | Shur et al. |
| 5,465,082 A | 11/1995 | Chaco |
| 5,471,404 A | 11/1995 | Mazer |
| 5,493,283 A | 2/1996 | Hopper et al. |
| 5,515,426 A | 5/1996 | Yacenda et al. |
| 5,534,876 A | 7/1996 | Erickson et al. |
| 5,541,585 A | 7/1996 | Duhame et al. |
| 5,548,637 A | 8/1996 | Heller et al. |
| 5,561,412 A | 10/1996 | Novak et al. |
| 5,572,195 A | 11/1996 | Heller et al. |
| 5,576,952 A | 11/1996 | Stutman et al. |
| 5,588,009 A | 12/1996 | Will |
| 5,594,786 A | 1/1997 | Chaco et al. |
| 5,610,589 A | 3/1997 | Evans et al. |
| 5,627,524 A | 5/1997 | Fredrickson et al. |
| 5,633,742 A | 5/1997 | Shipley |
| 5,689,229 A | 11/1997 | Chaco et al. |
| 5,695,091 A | 12/1997 | Winings et al. |
| 5,699,038 A | 12/1997 | Ulrich et al. |
| 5,732,711 A | 3/1998 | Fitzpatrick et al. |
| 5,742,233 A | 4/1998 | Hoffman et al. |
| 5,745,272 A | 4/1998 | Shipley |
| 5,774,865 A | 6/1998 | Glynn |
| 5,781,942 A | 7/1998 | Allen et al. |
| 5,793,653 A | 8/1998 | Segal |
| 5,793,861 A | 8/1998 | Haigh |
| 5,812,059 A | 9/1998 | Shaw et al. |
| 5,815,566 A | 9/1998 | Ramot et al. |
| 5,818,617 A | 10/1998 | Shipley |
| 5,822,418 A | 10/1998 | Yacenda et al. |
| 5,822,544 A | 10/1998 | Chaco et al. |
| 5,838,223 A | 11/1998 | Gallant et al. |
| 5,900,067 A | 5/1999 | Jones |
| 5,900,801 A | 5/1999 | Heagle et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,966,753 A | 10/1999 | Gauthier et al. |
| 6,009,333 A | 12/1999 | Chaco |
| 6,038,331 A | 3/2000 | Johnson |
| 6,125,482 A | 10/2000 | Foster |
| 6,133,837 A | 10/2000 | Riley |
| 6,147,592 A | 11/2000 | Ulrich et al. |
| 6,147,607 A | 11/2000 | Lynn |
| 6,195,588 B1 | 2/2001 | Gauthier et al. |
| 6,211,788 B1 | 4/2001 | Lynn et al. |
| 6,236,317 B1 | 5/2001 | Cohen et al. |
| 6,252,512 B1 | 6/2001 | Riley |
| 6,259,355 B1 | 7/2001 | Chaco et al. |
| 6,344,794 B1 | 2/2002 | Ulrich et al. |

FOREIGN PATENT DOCUMENTS

| | | |
|---|---|---|
| DE | 19903079 | 8/2000 |
| EP | 0 788 984 A1 | 8/1987 |
| EP | 0 543 763 A1 | 11/1992 |
| EP | 0 899 215 A1 | 3/1999 |
| FR | 2 705 952 | 6/1993 |
| FR | 2 753 183 | 9/1996 |
| GB | 2 193 359 | 2/1988 |
| GB | 2 230 365 | 10/1990 |
| GB | 2 265 038 | 9/1993 |
| GB | 2 356 482 | 5/2001 |

OTHER PUBLICATIONS

Introduction to Radio Frequency Identification, Intermec Technologies Corporation, © 1999 Amtech Systems Corporation.

http://www.currentdirections.com/hardware/zebra/r140/html, May 15, 2002.

http://www.rfidusa.com/rfid_zebra-r140printer.html, May 21, 2002.

http://www.rfidusa.com/rfid_introduction.html, May 21, 2002.

http://www.rapidttp.com/transponder/presre37.html, May 21, 2002.

"Great New Product: Infared Locator," Teleconnect, Feb. 1986.

T.H. Ooi, "Low Cost RF Identification and Locating System," IEEE Trans. On Consumer Electronics, vol. 35, No. 4, Nov. 1989, pp. 831-839.

United Identification Systems Corp., Intra-Com, 1989.

The Computer for the 21st Century, Mark Weiser, Scientific American, Sep. 1991.

Keeping Track of Alzhelmer and Dementia Prone Patients Just Got Easier, Security Tag Systems, Inc., 1991.

Infant Monitoring System, Sekurmed.

Department Waste Disposal Compliance Report

| Department: | OB/GYN | Date February 20, 2000 |
|---|---|---|
| Overall: | 20% Recycleable | |
| | 29% IMW | |
| | 51% General Waste | |
| Total Weight: | 100 lbs. | |
| Total Cost: | $12,472 | |

Department Breakdown

| Employee | Recyclables | IMW | General | Weight | Cost |
|---|---|---|---|---|---|
| Jones, M | 30% | 15% | 55% | 24 lbs. | 2,945 |
| Smith, A | 10% | 64% | 26% | 48 lbs. | 8,453 |
| Williams, S | 20% | 8% | 72% | 28 lbs. | 1,074 |

Fig. 18

WASTE SEGREGATION COMPLIANCE SYSTEM

CROSS REFERENCE TO RELATED APPLICATIONS

This application is a continuation of U.S. patent application Ser. No. 10/154,644, filed May 24, 2002, now U.S. Pat. No. 6,759,959, which claims the benefit of U.S. Provisional Patent Application Ser. No. 60/293,924, filed May 25, 2001, the disclosure of each is hereby expressly incorporated herein by reference.

BACKGROUND AND SUMMARY OF THE INVENTION

The present invention relates to a waste segregation compliance system and, in particular, to a waste segregation compliance system which monitors the quantity of various categories of waste, such as infectious medical waste, general waste and sharps, disposed of by individual persons.

Healthcare facilities attempt to minimize the spread of infection and contamination by providing waste receptacles to receive infectious medical waste (IMW). IMW is waste that requires special control and handling procedures thereby increasing disposal costs. Examples of IMW are blood, mucus, tissue, soiled surgical dressings, syringes, and other items which are exposed to potentially infectious agents.

A healthcare facility could substantially reduce its IMW disposal costs through proper waste segregation. More particularly, not all the waste which is disposed of as IMW is in fact IMW. As such, a healthcare facility can reduce IMW disposal costs by proper segregation of IMW from other types of waste, such as general waste and sharps, at the point of generation. However, several factors prohibit proper segregation of waste, such as inconvenience to the overworked healthcare provider, the timely location of the proper trash receptacles, and the lack of a monitoring and feedback system.

Accordingly, a need exists for a waste segregation compliance system, which provides an integrated waste receptacle, detects the disposal of various types and amounts of waste, determines the identity of the person depositing waste, and provides reporting capabilities. Additionally, a need exists for a waste segregation compliance system which automatically monitors waste disposal and provides reports detailing the compliance of individual persons and departments with waste disposal protocols.

BRIEF DESCRIPTION OF THE DRAWINGS

FIG. 18 is an illustrative example of a departmental waste disposal compliance report;

DETAILED DESCRIPTION OF THE DRAWINGS

Figure 1:
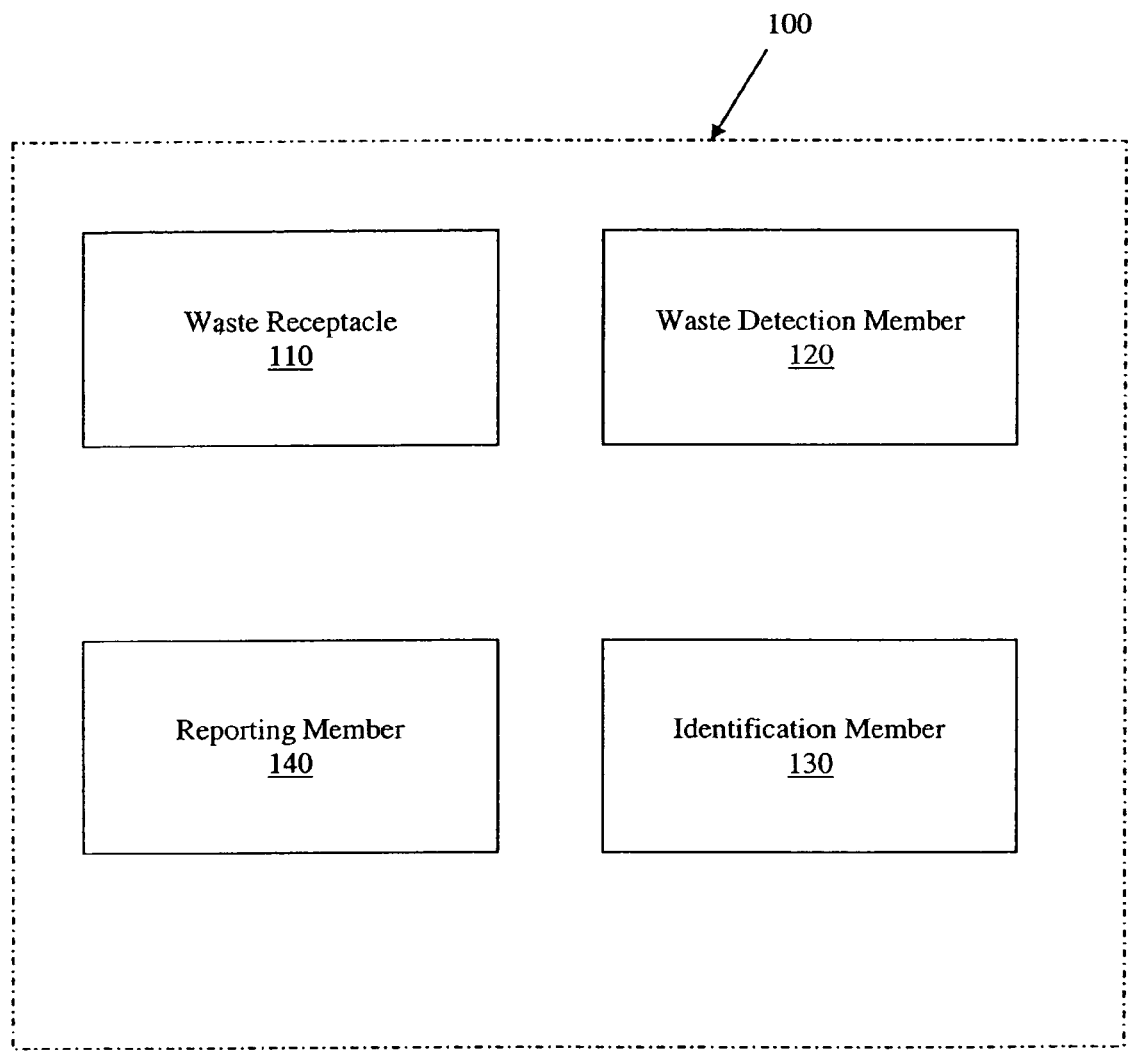
FIG. 1 is a diagrammatical block diagram illustrating the components of a waste segregation compliance system of the present invention.

While the invention is susceptible to various modifications and alternative forms, exemplary embodiments thereof have been shown by way of example in the drawings and will herein be described in detail. It should be understood, however, that there is no intent to limit the invention to the particular form disclosed, but on the contrary, the invention is to cover all modifications, equivalents, and alternatives falling within the spirit and scope of the invention as defined by the appended claims.

Figure 3:
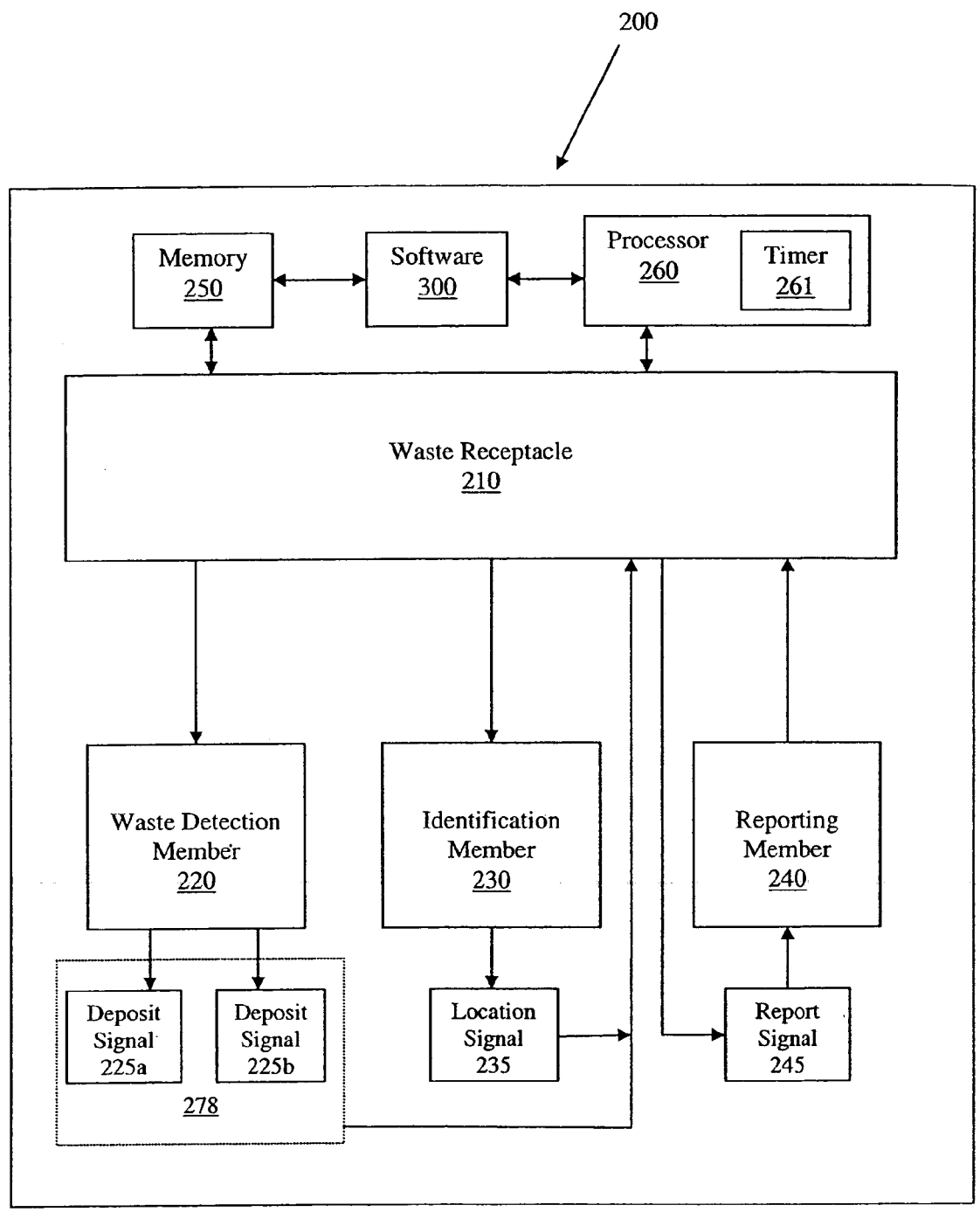
FIG. 3 is a diagrammatical block diagram illustrating the components of a first embodiment of the waste compliance system of the present invention.

The present invention is a waste segregation compliance system 100. In a general form as illustrated in FIG. 1, the waste segregation compliance system 100 monitors the placement of waste into a waste receptacle. In a first exemplary embodiment, the waste segregation compliance system 200 is a stand alone system (FIG. 3). In a second exemplary embodiment, the waste segregation compliance system 500 includes a caregiver locating and tracking system 501 (FIG. 10), which performs locating and tracking of individuals or assets in addition to the monitoring of waste placement. Caregiver locating and tracking systems are known in the art, as disclosed, for example, in U.S. Pat. Nos. RE35,035; 5,561,412; and 5,838,223, all of which are assigned to the assignee of the present invention, and the disclosures of which are expressly incorporated by reference herein.

Referring further to FIG. 1, waste segregation compliance system 100 is composed of a waste receptacle 110, a waste detection member 120, an identification member 130, and a reporting member 140. Waste receptacle 110 provides a holding place for waste until a later time when the waste can be properly disposed. Waste detection member 120 detects the use of waste receptacle 110 and may form part of receptacle 110 itself. Alternatively, waste detection member 120 may be provided separately from the waste receptacle 110. Examples of a use of waste receptacle 110 detectible by waste detection member 120 include the opening of a lid or cover, the deposit of waste into waste receptacle 110, the passing of waste through a threshold of waste receptacle 110, an increase or decrease in the weight of the waste contained in waste receptacle 110, and a change in the level or volume of the waste in waste receptacle 110.

Identification member 130 identifies a person adjacent to the waste receptacle 110. Identification member 130 may be coupled to the waste receptacle 110. Alternatively, identification member 130 may be positioned remotely from waste receptacle 110. Reporting member 140 is in communication with identification member 130, and is configured to report on various activities, such as the identity of the person adjacent the waste receptacle 110. Examples of the reporting of the identity of the person adjacent waste receptacle 110 by reporting member 140 include making available the identification information to a processor, displaying the identification information on a display screen and producing physical summaries of the identification information. In one exemplary embodiment, reporting member 140 is in communication with both identification member 130 and waste detection member 120 for reporting information related to both the identity of the person adjacent waste receptacle 110 and the amount of waste placed into waste receptacle 110. In another exemplary embodiment, reporting member 140 computes and reports the disposal cost associated with the amount of waste placed in waste receptacle 110.

Figure 2:
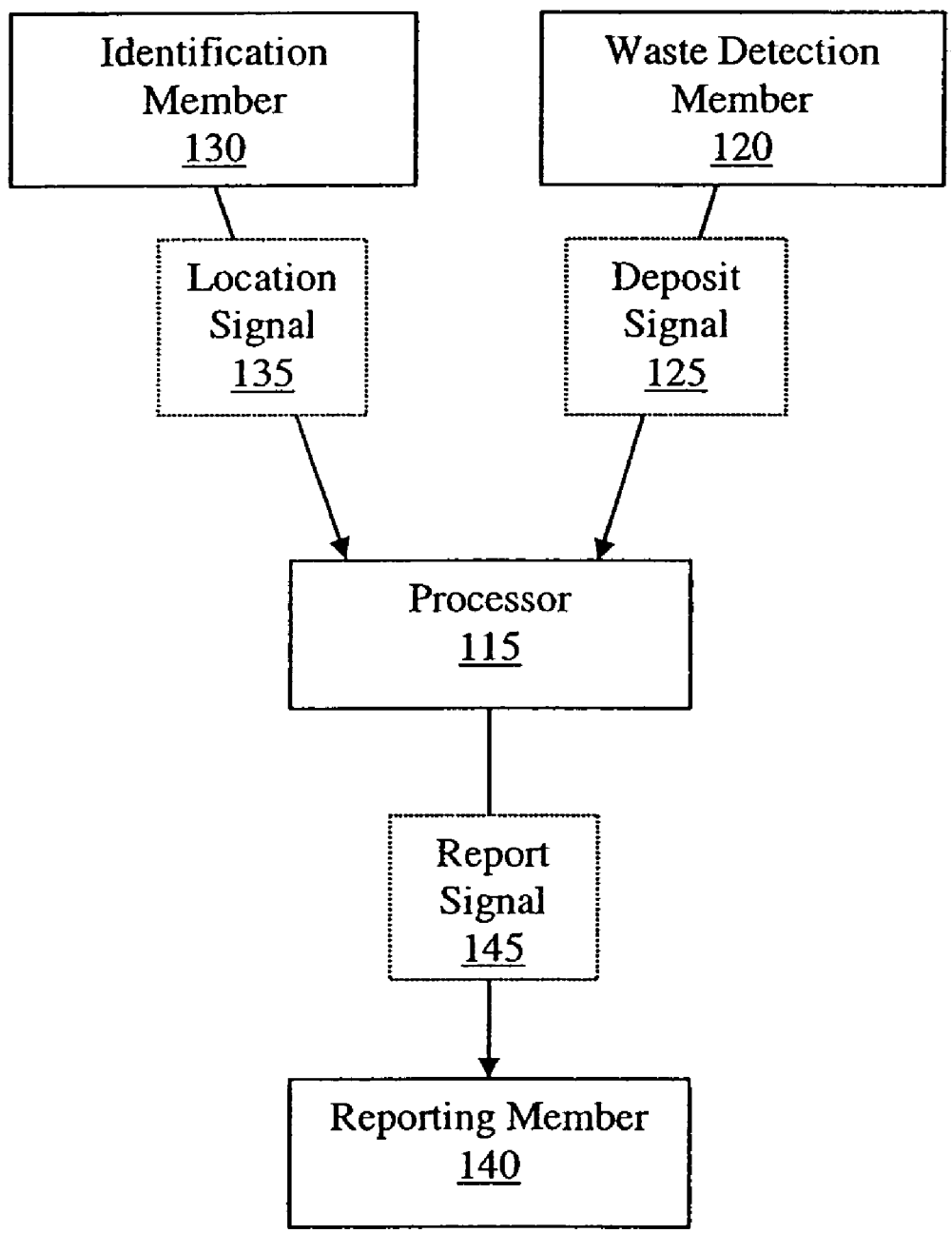
FIG. 2 is a block diagram illustrating the relationship between a sub-set of the components of FIG. 1.

FIG. 2 further illustrates the interaction between waste detection member 120, identification member 130 and reporting member 140 of waste segregation compliance system 100. Referring to FIG. 2, waste detection member 120 detects a use of waste receptacle 110 and generates a deposit signal 125 in response to the detected use. Identification member 130 detects the presence of a person adjacent to waste receptacle 110 and generates a location signal 135 in response to the detected presence. Deposit signal 125 and location signal 135 are provided to a processor 115. In one exemplary embodiment, processor 115 is coupled to waste receptacle 110. In another exemplary embodiment, processor 115 is remote from waste receptacle 110. Processor 115 creates a report signal 145 in response to receiving deposit signal 125 and location signal 135. Report signal 145 is used by reporting member 140 to generate a report. In one exemplary embodiment, report signal 145 includes only location signal 135 because deposit signal 125 is not provided. In another exemplary embodiment, report signal 145 includes only deposit signal 125 because location signal 135 is not provided.

Turning to FIG. 3, the stand-alone waste segregation compliance system 200 is shown. In waste segregation compliance system 200, a waste detection member 220 which generates a deposit signal 225, an identification member 230 which generates a location signal 235, and a reporting member 240 which receives a report signal 245, are provided in communication with a waste receptacle 210. It should be appreciated that waste detection member 220, identification member 230, and reporting member 240 may be integrated with waste receptacle 210 or, alternatively, may be positioned spaced from waste receptacle 210. Waste receptacle 210 additionally is coupled to a memory 250 and a processor 260. Processor 260 is in communication with memory 250 and includes a timer or clock 261.

Figure 4:
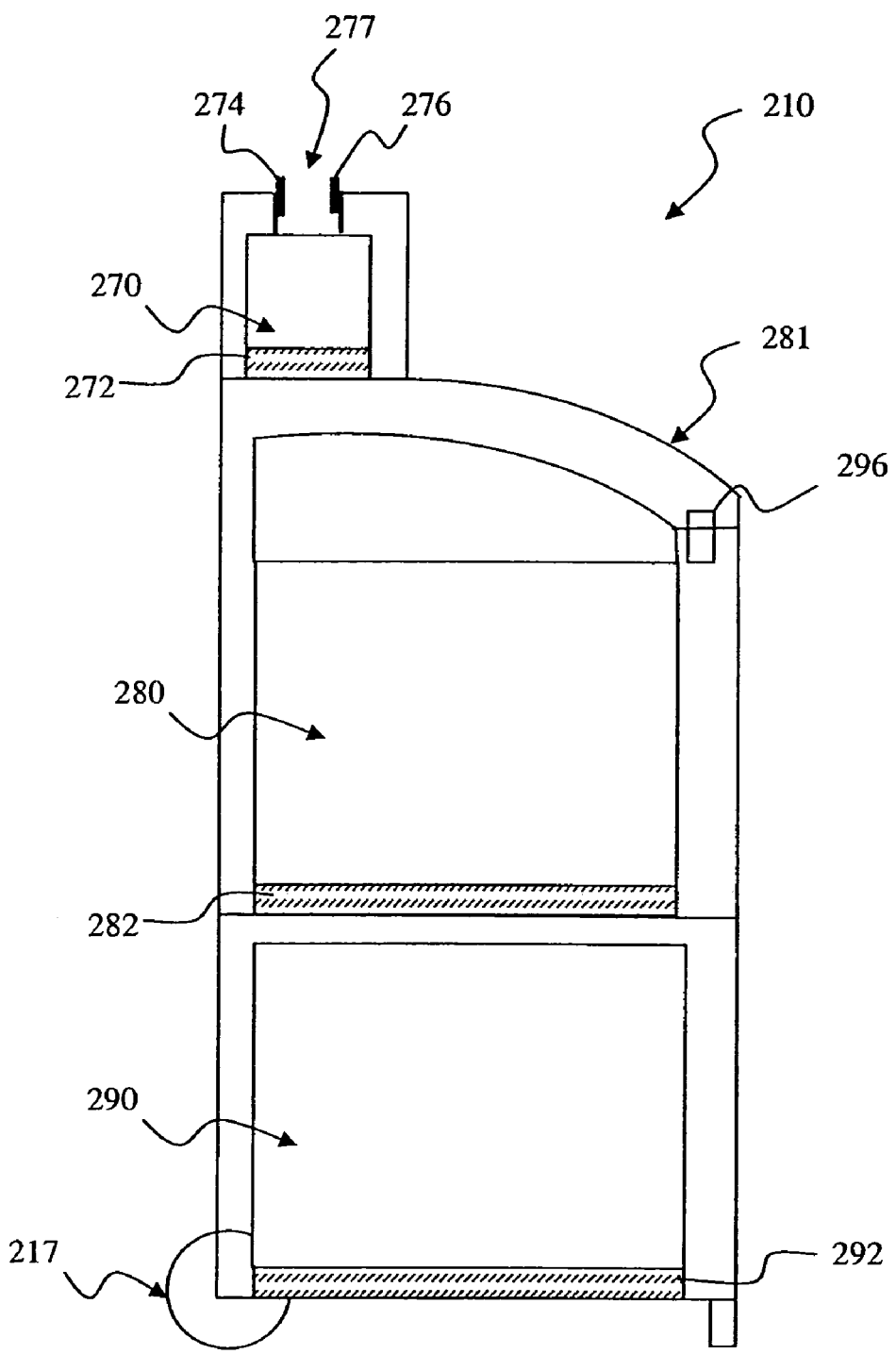
FIG. 4 is a diagrammatical, side view of a waste receptacle of the present invention.
Figure 4A:
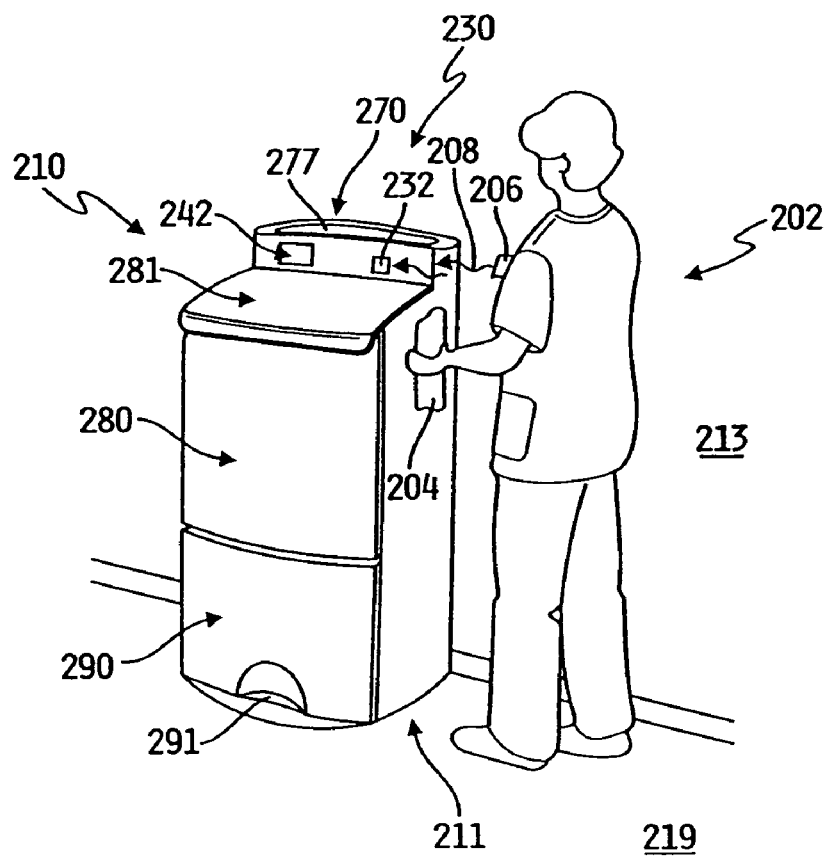
FIG. 4A is a perspective view of the waste receptacle of FIG. 4.

As shown in FIG. 4A, a person 202 approaches a housing 211 of waste receptacle 210 with waste 204. A badge 206 is associated with person 202. An illustrative embodiment of badge 206 includes an infrared (IR) transmitter which transmits an identification signal 208 including a unique identification code specific to the person 202 wearing badge 206. While the transmitter in each badge 206 is described as an infrared (IR) transmitter, it is within the scope of the invention as presently perceived to include transmitters that transmit any desired frequency of electromagnetic radiation or sound waves, so long as, identification member 230 is compatible therewith and capable of detecting such transmissions.

In FIG. 4A, identification member 230 includes a detector 232 to detect identification signal 208. It is well known in the art to determine an identification code from a received identification signal 208 which was originally transmitted with the identification code. It is within the scope of the present invention for badge 206 to include a receiver, such that identification member 230 is able to poll or interrogate badge 206, thereby causing badge 206 to transmit identification signal 208. In an exemplary embodiment, identification member 230 includes a transmitter which sends a polling signal to badge 206. In response to the reception of the polling signal, badge 206 sends identification signal 208 to identification member 230.

In an alternative embodiment, identification member 230 includes a conventional keypad (not shown) whereby person 202 manually inputs his or her identification code into the keypad. In a further alternative embodiment, identification member 230 includes a magnetic strip reader (not shown) of the type known in the art. Person 202 provides his or her identification code to identification member 230 by swiping a conventional identification card (not shown), having a magnetic strip encoded with the identification code, through the magnetic strip reader.

As will be further described below, in an alternative embodiment, badge 206 includes an RFID tag for providing ID signal 208 to detector 232. Accordingly, detector 232 includes a transceiver for activating the RFID tag of badge 206, and for receiving ID signal 208.

Figure 4B:
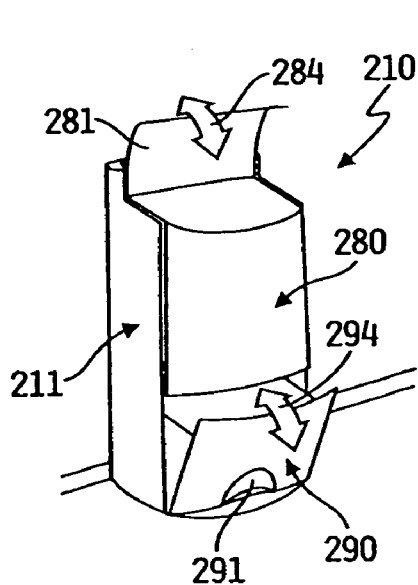
FIG. 4B is a perspective view of the waste receptacle of FIG. 4A, illustrating the operation of the waste receptacle.
Figure 4C:
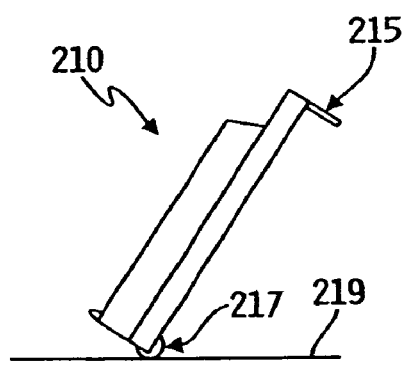
FIG. 4C is a side view of the waste receptacle of FIG. 4A.

The exemplary waste receptacle 210, shown in FIGS. 4 through 4C includes separate or segregated waste compartments 270, 280, and 290. By having multiple compartments 270, 280, and 290, different types of waste can be segregated based upon waste type. In an exemplary embodiment for use in a healthcare facility, compartment 270 is designated for sharps waste such as needles, compartment 290 is designated for infectious medical waste (IMW) such as soiled surgical dressings and syringes, and compartment 280 is designated for general waste, such as any waste not designated for compartments 270 or 290.

It is not a requirement that compartments 270, 280, and 290 all be contained within single housing 211. In one embodiment, compartment 270 is located on a wall 213 and compartments 280 and 290 are located in a floor receptacle. Identification member 230 and waste detection member 220 must be able to provide location signal 235 and deposit signal 225 such that report signal 245 is generated, regardless of the physical placement of compartments 270, 280 and 290. It is within the scope of the present invention to assign different types of waste to compartments 270, 280 and 290, and to vary the number of compartments. In one exemplary embodiment, waste receptacle 210 includes a single compartment. A single compartment arrangement is advantageous when only a single type of waste is to be tracked. Applications requiring that only a single type of waste be tracked generally occur when disposal costs are substantially uniform for different types of waste except for one type of waste which has a disposal cost substantially different from that of other types of waste.

Referring to FIGS. 4 and 4A, waste 204 is placed into compartment 270 by passing waste 204 through a threshold or opening 277. Waste 204 is placed into compartment 280 by lifting a pivotally mounted lid or covering 281, as shown in FIG. 4B by arrow 284. Waste 204 is placed in compartment 290 by applying pressure to a foot pedal 291 which causes a bin 293 of compartment 290 to tilt or pivot forward, as indicated by arrow 294 in FIG. 4B. While the compartment 290 includes a bin 293 pivotally supported by the housing 211, it should be appreciated that the compartment 290 may be configured to provide access in a variety of manners, including, but not limited to, a sliding bin and a pivotally mounted access door.

Waste detection member 220 detects when waste 204 is deposited in one of or a combination of compartments 270, 280 and 290. Compartments 270, 280, and 290, in an exemplary embodiment, contain sensors, such as scales 272, 282, and 292 (FIG. 4), to detect a change in the weight of the respective compartment. In this exemplary embodiment, waste detection member 220 determines the compartment 270, 280 or 290 into which waste 204 was deposited by determining the change in weight for each respective compartment 270, 280 and 290.

In the exemplary embodiment of FIG. 4, waste detection member 220 includes threshold components 274 and 276 positioned near opening 277 in compartment 270. Components 274 and 276 are designed to determine when waste 204 passes into opening 277 and can be used in place of scale 272 or in combination therewith. In one embodiment, component 274 is an emitter and component 276 is a detector configured to detect energy emitted by component 274. When waste 204 passes between emitter 274 and detector 276 the signal detected by detector 276 from emitter 274 is modified, thereby indicating that waste 204 is being placed in compartment 270.

In the exemplary embodiment of FIG. 4, waste detection member 220 includes a sensor 296 associated with covering 281 to detect the deposit of waste 204 into compartment 280 by detecting the opening of covering 281. The sensor 296 may be utilized in place of scale 282 or in combination therewith. Examples of sensors to detect the opening of cover 281 include inductive based sensors or continuity sensors.

In the another exemplary embodiment, waste detection member 220 includes sensors (not shown) to detect the level or volume of the waste 204 in compartments 270, 280 and 290. Such level or volume sensors are known in the art and are especially tailored for use with applications which include liquid waste. An advantage of sensors 272, 282, and 292 over threshold components 274, 276 and sensor 296 associated with the opening of cover 281, is that sensors 272, 282, and 292 not only detect the deposit of waste 204 into compartments 270, 280 and 290, respectively, but additionally detect the weight of waste 204 deposited.

Referring further to the exemplary embodiment waste receptacle 210 of FIG. 4A, reporting member 240 includes a display screen 242. As explained in more detail below with reference to FIGS. 5–7, when waste compliance system 200 detects the deposit of waste 204 into compartment 270, 280 or 290 of waste receptacle 210 and identifies the person 202 adjacent waste receptacle 210, then reporting member 240 reports the results of the detections. Generally, waste detection member 220 generates deposit signal 225 and identification member 230 generates location signal 235. Deposit signal 225 and location signal 235 are combined to generate report signal 245 which is made available to reporting member 240. In another exemplary embodiment, report signal 245 contains only location signal 235, such that reporting member 240 reports location signal 235 based on identification signal 208, but not deposit signal 225. In another exemplary embodiment, report signal 245 contains only deposit signal 225, such that, reporting member 240 reports deposit signal 225 but not location signal 235.

Figure 8:
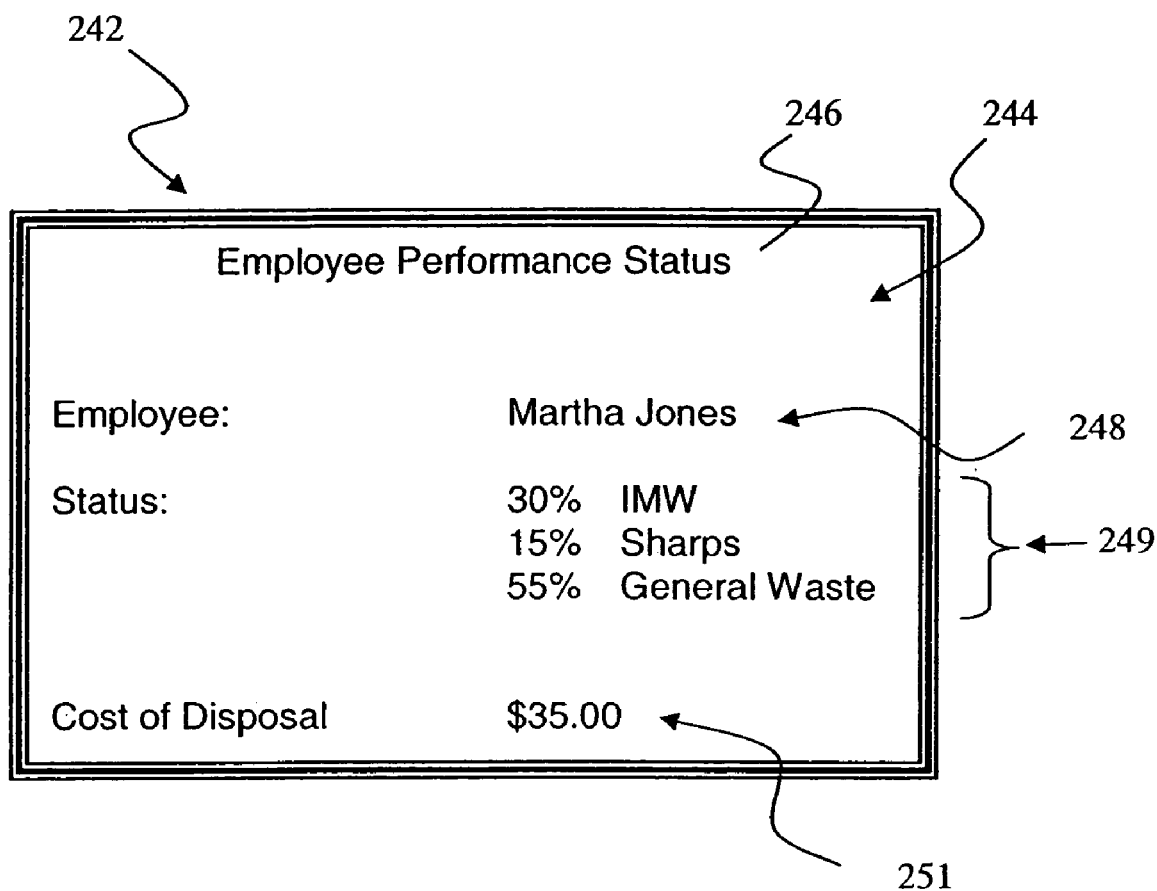
FIG. 8 is a sample waste receptacle display report.

In FIG. 8, an illustrative report 244 is shown of the type for presentation on display 242. Report 244 includes a title 246, a name or other identifying information 248 of person 202, a breakdown 249 of waste 204 deposited and a calculated disposal cost 251.

Referring again to FIG. 4C, waste receptacle 210 further includes a handle 215 and wheels 217. Wheels 217 are rotatably supported at a lower rear end of housing 211, while handle 215 is located at an upper rear end of housing 211 and extend outwardly. The wheels 217 provide a pivot axis about which the housing 211 may be tilted. In one embodiment, handle 215 is pivotally mounted for storage within a recess (not shown) of housing 211 when waste receptacle 210 is in use. Handle 215 and wheels 217 allow for the easy transport of waste receptacle 210 from location to location. Waste receptacle 210 is moved, similar to a two-wheel cart, by tilting housing 211 backwards, such that only wheels 217 contact the floor 219, and then rolling waste receptacle 210 either forward or backward on wheels 217.

The mobility of waste receptacle 210 allows for waste receptacle 210 to be moved to a conventional central disposal location where compartments 270, 280 and 290 are emptied into corresponding larger compartments. Alternatively, the mobility of waste receptacle 210 allows person 202 to take waste receptacle 210 with them during their work shift. For example, in an industrial setting, person 202 may transport waste receptacle 210 with them during the performance of preventive maintenance operations to machines thereby facilitating the proper segregation of waste, such as old parts, used fluids and general waste.

Figure 5:
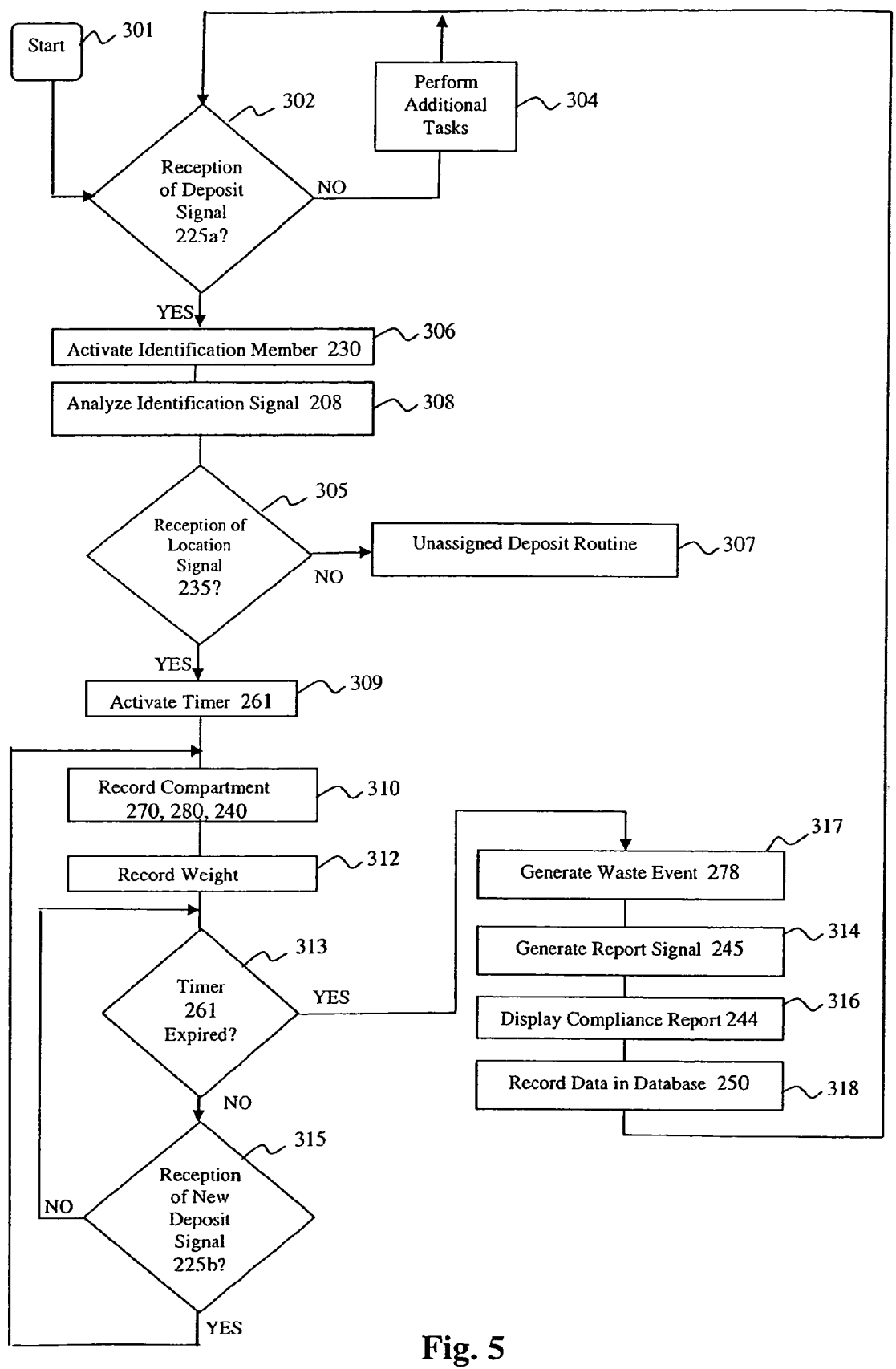
FIG. 5 is a flowchart representation of the steps performed by a first component of the software of the waste segregation compliance system of FIG. 3.
Figure 6:
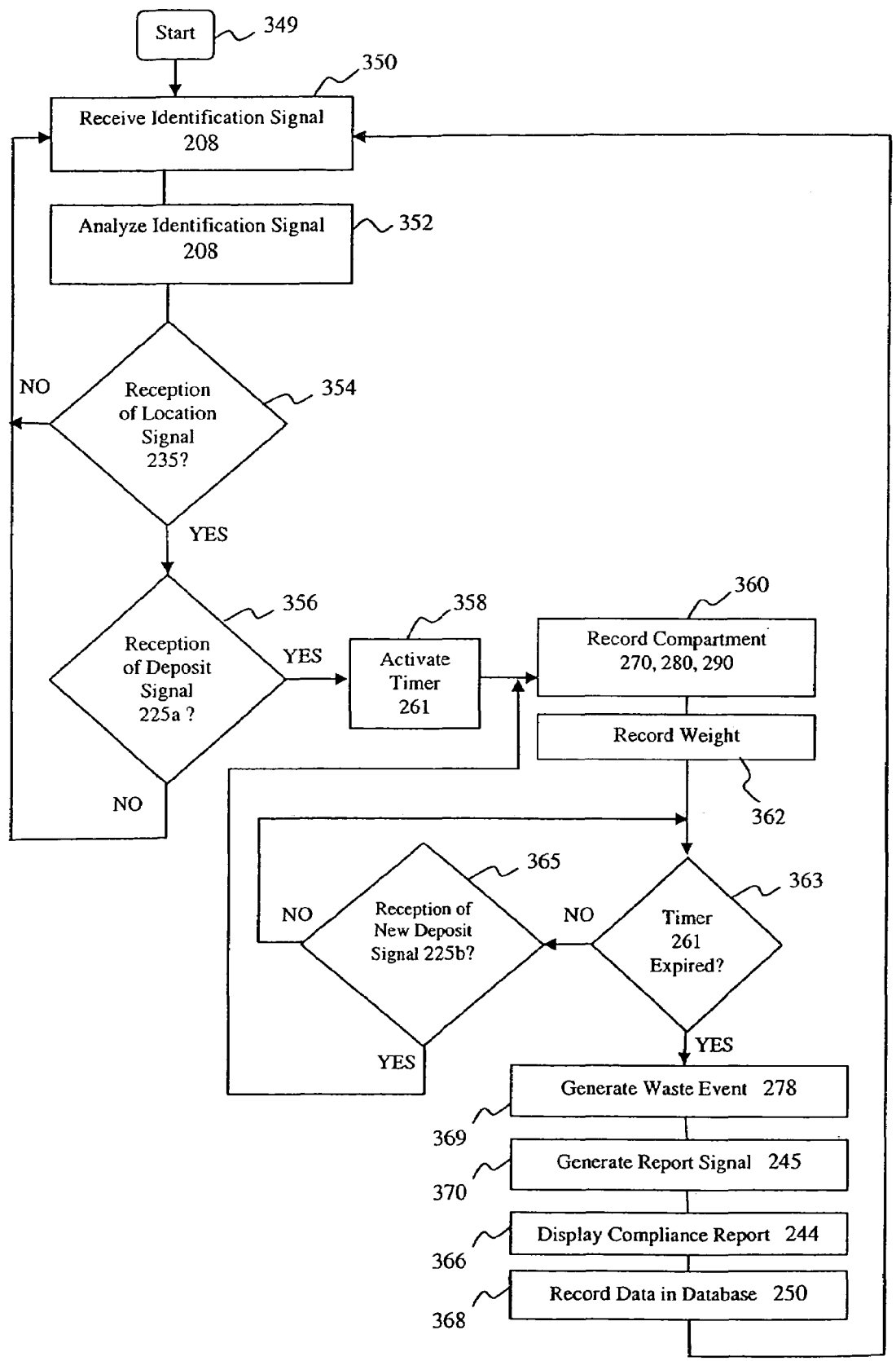
FIG. 6 is a flowchart representation of the steps performed by a second component of the software of the waste segregation compliance system of FIG. 3.
Figure 7:
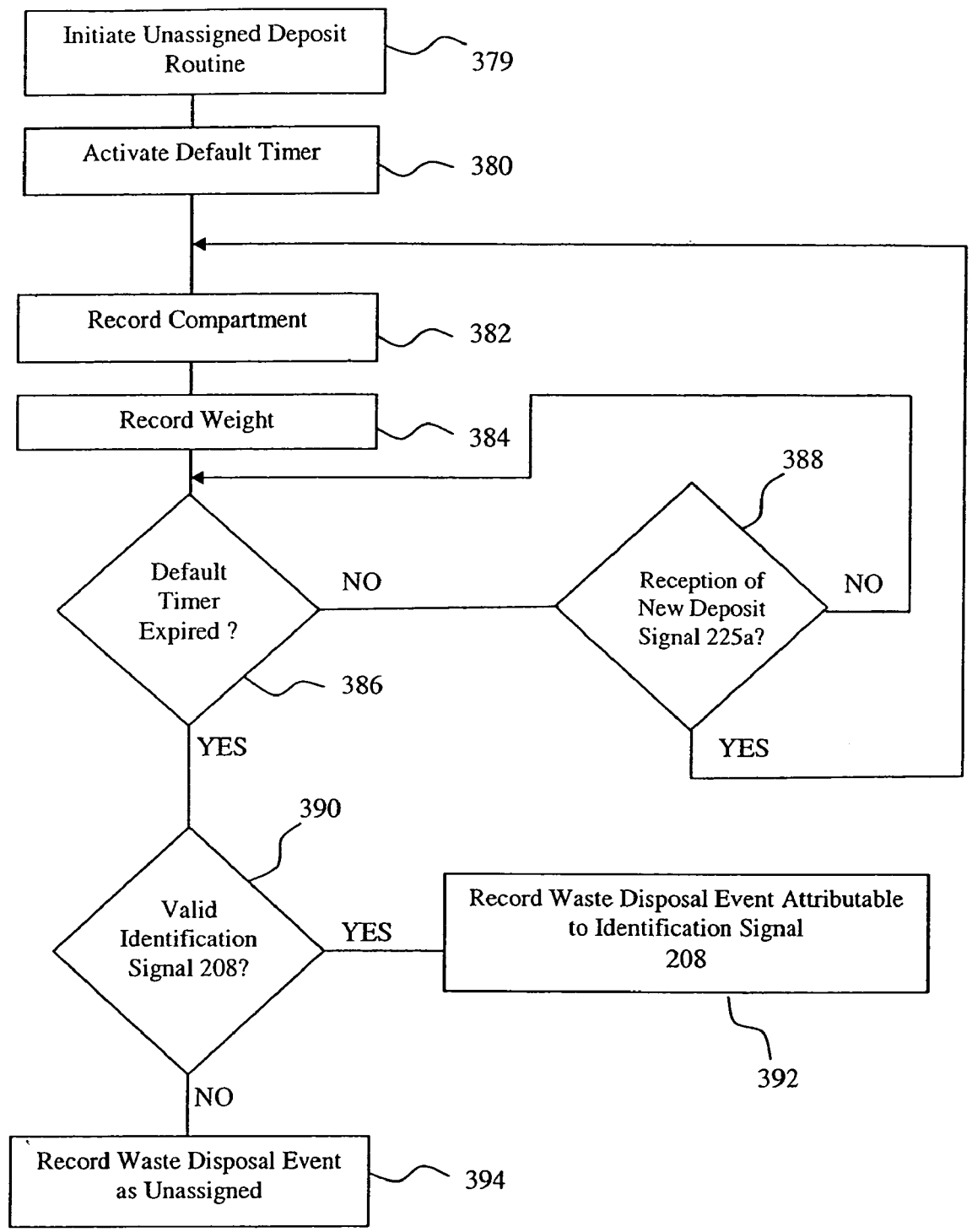
FIG. 7 is a flowchart representation of the steps performed by the software of the waste segregation compliance system of FIG. 3 in the absence of receiving a valid identification signal.

Referring to FIGS. 4 and 5–7, the operation of waste detection member 220, identification member 230 and reporting member 240 is controlled by processor 260 which executes software 300. Flowcharts corresponding to two components of software 300 executed by processor 260 are shown in FIGS. 5 and 6. The first component of software 300 is executed when deposit signal 225 is generated within a reasonable time prior to a location signal 235. The length of time which is considered a reasonable time is a variable set based upon (i) the type of identification member 230, (ii) the type of waste detection member 220, and (iii) the requirements of the accompanying tasks, for example patient care. The second component of software 300 is executed when location signal 235 is generated within a reasonable time prior to deposit signal 225. A reasonable time may be based upon the factors identified above. Each component of software 300 is detailed below with reference to FIGS. 5 and 6. FIG. 7 illustrates the steps taken by software 300 when a valid identification signal 208 is not received by identification member 230 and therefore location signal 235 is not generated within a reasonable time after the reception of deposit signal 225.

A flowchart illustrating the steps or functions performed by the first component of software 300 is shown in FIG. 5. Once the system 200 is activated at block 301, all variables are initialized or set to initial values. More particularly, the amount, typically the weight, of waste 204 in each compartment 270, 280, 290 is measured and stored in memory 260. Next, software 300 waits to receive deposit signal 225*a* from waste detection member 220, as represented at block 302. As detailed above, deposit signal 225 represents the detection of waste 204. In an exemplary embodiment, software 300 is capable of performing additional tasks in the absence of the reception of deposit signal 225*a*, as represented by block 304. For example, the additional tasks are initiated by an interrupt to the software execution. One example of an additional task, is the processing of location signal 235 in the absence of deposit signal 225*a* (see FIG. 6). If deposit signal 225*a* is received, then software 300 activates identification member 230.

Block 306 represents the activation of waste receptacle detector 232 in response to waste 204 being detected by waste detection member 220. As detailed above, waste receptacle detector 232 detects the identification signal 208 emitted by badge 206. The received identification signal 208 is analyzed to determine the identity of person 202, at process block 308. If identification signal 208 is valid in accordance with predetermined criteria, then identification member 230 generates a location signal 235. If identification signal 208 is not valid, then identification member 230 does not generate a location signal 235. In an alternative embodiment, identification member 230 is continuously active, such that location signal 235 is generated independent of the generation of deposit signal 225*a*. By having identification member 230 always active, waste segregation compliance system 200 is capable of tracking the identity of person 202 adjacent detector 232, regardless of whether person 202 deposits wastes 204 within waste receptacle 210.

After a reasonable time has passed, software 300 checks to determine if a valid location signal 235 has been received from identification member 230, as represented at decision block 305. If a location signal 235 has not been received, then software 300 initiates an unassigned deposit routine, as represented at process block 307. The unassigned deposit routine is explained in detail below in connection with FIG. 7. If a valid location signal 235 is received, then software 300 activates timer 261 at block 309. The timer 261 controls the predetermined time frame or period wherein multiple deposits of waste 204 are all included in a single waste event 278 and attributed to the same person 202 identified in location signal 235. Waste event 278 includes all of the deposit signals 225 received during the period of time defined by the timer 261. For example, in FIG. 3 two separate waste deposit signals 225*a* and 225*b* generated during a period of time defined by timer 261 are grouped together as a single waste event 278 for transmission to processor 260. By setting the timer 261 to a low or zero value, each deposit of waste 204 is recorded as a separate waste event 278. By increasing the timer 261 to a higher value, multiple deposit signals 225 are included in the same event. The compartment 270, 280, 290 corresponding to the detected deposit signal 225 is recorded within memory 250 at block 310, and the weight of the contents of identified compartment 270, 280, 290 is recorded within memory 250 at block 312.

As is readily apparent, the current recorded weight of waste 204 within any compartment 270, 280 and 290 is a composite value of previously deposited waste 204. The software 300 is therefore capable of calculating the incremental change in weight due to the addition of new waste 204 into a respective compartment 270, 280 and 290. More particularly, the memory 250 stores a value for weight of waste 204 at a given time. After additional waste 204 is added to the respective compartment 270, 280 and 290, the processor 260, as instructed by software 300, determines a differential between the new weight of the compartment 270, 280 and 290 and the weight stored in memory 250. As such, the weight of the new additional waste 204 is efficiently calculated.

Software 300 determines if the timer 261 expired at block 313. If the timer 261 has not expired, then at block 315 software 300 determines if an additional deposit signal 225*b* has been generated by waste detection number 220. If an additional deposit signal 225*b* has been received, then the process returns to block 310 where the compartment 270, 280, 290 corresponding to the deposit signal 225*b* is recorded. The weight of the compartment 270, 280, 290 is again recorded at bock 312.

In another exemplary embodiment, software 300 records the weight of each compartment 270, 280, 290 only after the timer 261 has expired. As such, the total weight of waste 204, corresponding to the detected deposit signals 225, is recorded after the timer 261 has expired. In such a system, deposit signal 225 serves only as an indication of which compartments 270, 280, 290 are to be weighed.

Once the timer 261 has expired, as determined at decision block 313, software 300 generates waste event 278 as indicated in block 317. Waste event 278 is a summary of all deposit signals 225 received prior to the expiration of the timer 261 and includes the compartment 270, 280, and 290 into which waste 204 was deposited and the amount of waste deposited. Report signal 245 is generated by software 300 and sent to reporting member 240 at block 314. Report signal 245 includes information from location signal 235 and waste event 278.

Reporting member 240 communicates a compliance report 244 created from report signal 245. In one exemplary embodiment, compliance report 244 is displayed on display 242 as illustrated at block 316. In another exemplary embodiment, a tangible or hard copy of compliance report 244 is created with an appropriate output device, such as a printer (not shown). In yet another exemplary embodiment, the data comprising compliance report 244 is made available in an electronic format to a database or e-mail system, such that the data can be provided to personnel or other software programs.

An example compliance report 244 is shown in FIG. 8. Compliance report 244 illustratively includes title 246, name or other identification 248 of person 202, waste breakdown 249 and disposal cost 251. The percentage of the overall waste 204 deposited in each compartment, 270, 280, 290 is included in waste breakdown 249. The disposal cost is figured by multiplying the weight of each type of waste 204 deposited by the average unit cost for disposing of that type of waste 204. The disposal costs for each type of waste 204 are then added together to provide an overall disposal cost. The average unit disposal costs for each type of waste 204 are variable values stored in memory 250 and accessed by software 300. Alternatively, compliance report 244 does not include disposal cost 251. The data detected is stored in a database or other file memory 250, as illustrated at block 318. In one exemplary embodiment, report signal 245 is stored in memory 250, along with the weight of each compartment 270, 280 and 290.

The timer 261 of blocks 309 and 313 of FIG. 5 provides person 202 with a fixed duration of time before software 300 records waste disposal event 278. If the span of time between two or more deposits of waste 204 and the corresponding reception of two or more deposit signals 225 is within the fixed duration of time set by the timer 261, then a single waste disposal event 278 is recorded when the timer 261 expires. If the span of time between any two time adjacent deposits of waste 204 and corresponding deposit signals 225 exceeds the fixed duration of time set by timer 261, then two waste disposal events 278 are recorded, one for each deposit.

In another exemplary embodiment, software 300 determines whether person 202 is still detected by detector 232 to set the time frame of waste event 278 thereby eliminating the need for timer 261. If identification signal 208 is still being received by detector 232, software 300 continues to monitor and record compartments 270, 280, 290 and weights of waste 204. Once identification signal 208 is no longer received by detector 232, software 300 generates waste event 278 and generates report signal 245.

A flowchart illustrating the steps or functions performed by the second component of software 300 is shown in FIG. 6. After activation of the system 200 at block 349, all variables are initialized or set to initial values. More particularly, the amount, typically the weight, of waste 204 in each compartment 270, 280, 290 is measured and stored in memory 250. When a user 202 is in proximity to waste receptacle 210, an identification signal 208 is received by identification member 230 at block 350. More particularly, detector 232 detects the presence of person 202 through reception of identification signal 208. The identification signal 208 is next analyzed, at process block 352. If identification signal 208 is valid, then identification member 230 generates a location signal 235. If identification signal 208 is not valid, then identification member 230 does not generate a location signal 235.

The software 300 at decision block 354 determines whether processor 260 has received location signal 235 from identification member 230. If the location signal 235 has been received by processor 260 then the software 300 continues at decision block 356, otherwise the process returns to block 350. At block 356 software 300 determines if waste detection member 220 has generated a deposit signal 225. If waste 204 has not been detected, software 300 loops back to block 350 and waits for the reception of a second, in time but not necessarily unique, location signal 235.

If a deposit signal 225a is received at block 356, software 300 actuates timer 261 at block 358. Next, the software 300 records within memory 250 the compartment 270, 280, 290 corresponding to deposit signal 225a, at block 360, and determines and records within memory 250 the weight of the contents of the identified compartment 270, 280, 290 at block 362.

Software 300 determines if the timer 261 has expired at decision block 363. If the timer 261 has not expired, then software 300 determines if an additional deposit signal 225b has been generated by waste detection member 220 at decision block 365. If an additional deposit signal 225b has been received by processor 260, then the process returns to block 360. The compartment 270, 280, 290 corresponding to the deposit signal 225b and the weight of respective compartments 270, 280, 290 are recorded, as represented by blocks 360 and 362.

In another exemplary embodiment, software 300 records the weight of each compartment 270, 280, 290 only after the timer 261 has expired. As such, the total weight of waste 204, corresponding to the received deposit signals 225, is recorded after the timer 261 has expired. In such a configuration, deposit signal 225 serves only as an indication of which compartment 270, 280, 290 is to be weighed.

Once the timer 261 has expired, as determined at block 363, software 300 generates waste event 278 at process block 369. Waste event 278 is a summary of all deposit signals 225 received prior to the expiration of the timer 261 and includes the compartment 270, 280, and 290 into which waste 204 was deposited and the amount of waste 204 deposited. Software 300 next instructs the processor 260 to generate and transmit report signal 245 to reporting member 240, as illustrated by block 370. Report signal 245 includes information from location signal 235 and waste event 278. The timer 261 illustrated in FIG. 6 provides person 202 with a fixed duration of time before software 300 records a waste disposal event 278.

In an alternative embodiment, software 300 determines whether identification signal 208 is still being received by detector 232 to set the time frame of waste event 278 thereby eliminating the need for timer 261. If identification signal 208 is still being received by detector 232, software 300 continues to monitor and record compartments 270, 280, 290 and weights of waste 204. Once identification signal 208 is no longer received by detector 232, software 300 generates waste event 278.

Reporting member 240 communicates compliance report 244 which was created from report signal 245. In one exemplary embodiment, at block 366 compliance report 244 is displayed on display 242. In another exemplary embodiment, a tangible or hard copy of compliance report 244 is created with an appropriate output device, such as a printer (not shown). In yet another exemplary embodiment, the data comprising compliance report 244 is made available in an electronic format to a database or e-mail system, such that the data can be provided to personnel or other software programs. An example of the compliance report 244 is described in detail above in connection with FIG. 8. The detected data is then stored in a database or file of memory 250, as illustrated at block 368. In an exemplary embodiment, the data stored in memory 250 includes the weight of compartments 270, 280, 290 and report signal 245.

FIG. 7 illustrates the unassigned deposit routine, which records a waste event 278 in the absence of the reception of a location signal 235. The unassigned deposit routine is initiated at block 379 from the software component illustrated in FIG. 5 when a deposit signal 225 has been received and a reasonable time has passed without the reception of a location signal 235. The term reasonable time is defined by a variable in software 300 and varies for different applications. In an exemplary embodiment, the variable corresponding to a reasonable time is set at 1 second.

Software 300 at block 380 activates a default timer (not shown) which is in addition to the timer 261 discussed in relation to FIGS. 5 and 6. Software 300 records into memory 250 the compartment 270, 280, 290 into which waste 204 is deposited, as represented by block 382. The software 300 further records into memory 250 the weight of waste 204, as represented by block 384. Software 300 determines if the default timer has expired, at decision block 386. If the default timer has not expired, then software 300 awaits an additional deposit of waste 204 into waste disposal event 278 and corresponding new deposit signal 225b at block 388. When the default timer expires, software 300 determines if identification member 230 has received a valid identification signal 208 and has generated location signal 235, as illustrated by block 390. If location signal 235 has been generated, then waste disposal event 278 is attributable to the person 202 identified by location signal 235, and such information is stored within memory 250 as indicated at block 392. If a location signal 235 is not received, then waste disposal event 278 is marked as unassigned at block 394.

Figure 9:
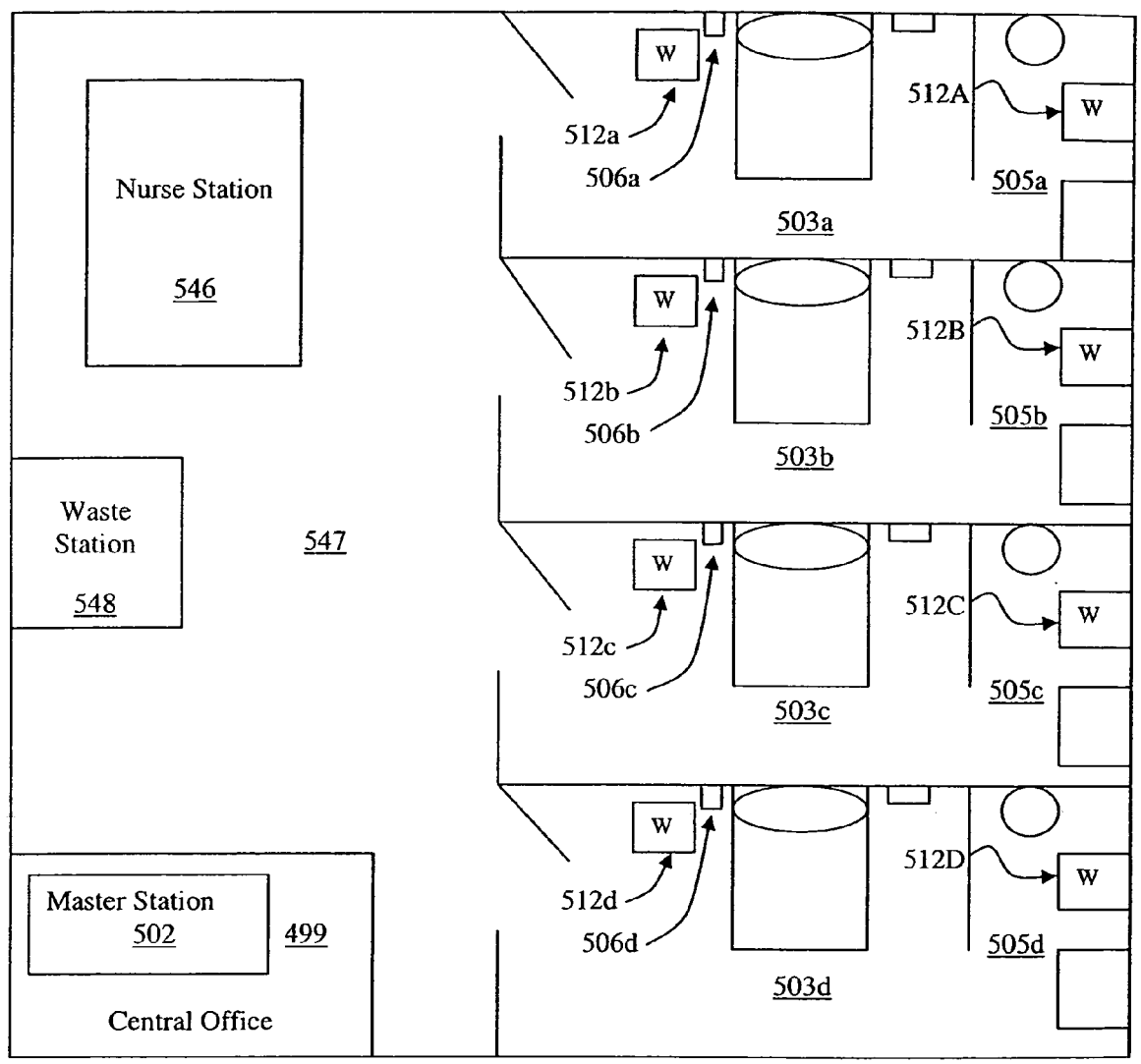
FIG. 9 is a diagrammatical representation of a portion of a healthcare facility incorporating a waste segregation compliance system of the present invention.

Referring now to FIGS. 9–16, a second illustrative embodiment of the waste segregation compliance system 500 is shown. Waste segregation compliance system 500 includes a locating and tracking system 501 to track the location of personnel in addition to monitoring waste disposal. A diagrammatical representation of a portion of a healthcare facility incorporating a waste segregation compliance system 500 is shown in FIG. 9. The healthcare facility includes a plurality of patient rooms 503a, 503b, 503c, and 503d. Each patient room 503a, 503b, 503c, and 503d includes a detector 506a, 506b, 506c, and 506d, respectively. Detectors 506a, 506b, 506c, and 506d are part of the caregiver locating and tracking system 501, the operation of which is explained in more detail below. Each illustrative patient room 503a, 503b, 503c, and 503d further includes one waste receptacle 512a, 512b, 512c, and 512d, respectively. Additional waste receptacles 512e, 512f, 512g, and 512h are located in illustrative patient restrooms 505a, 505b, 505c and 505d, respectively. For the remainder of this description, illustrative patient rooms 503a, 503b, 503c, and 503d shall be referred to generally as patient room 503, illustrative patient restrooms 505a, 505b, 505c and 505d shall be referred to generally as patient restroom 505, detectors 506a, 506b, 506c, and 506d shall be referred to generally as detector 506, and waste receptacles 512a, 512b, 512c, 512d, 512e, 512f, 512g, and 512h shall be referred to generally as waste receptacle 512, unless clarity dictates the need to refer otherwise.

It should be appreciated that patient room 503 is shown to include a single waste receptacle 512 for illustrative purposes only, and that the waste segregation compliance system 500 of the present invention finds applicability regardless of the number of such waste receptacles. For example, some patient rooms 503 may include no waste receptacles 512, some patient rooms 503 may include one waste receptacle 512, and some patient rooms 503 may include two or more waste receptacles 512. The operation of waste receptacle 512 and the interaction between waste receptacle 512 and caregiver locating and tracking system 501 is explained in greater detail below. The healthcare facility further includes a nurse station 546, a common area 547, a waste station 548 and a central office 499. The central office 499 includes a master station 502, which is a component of the locating and tracking system 501.

Figure 10:
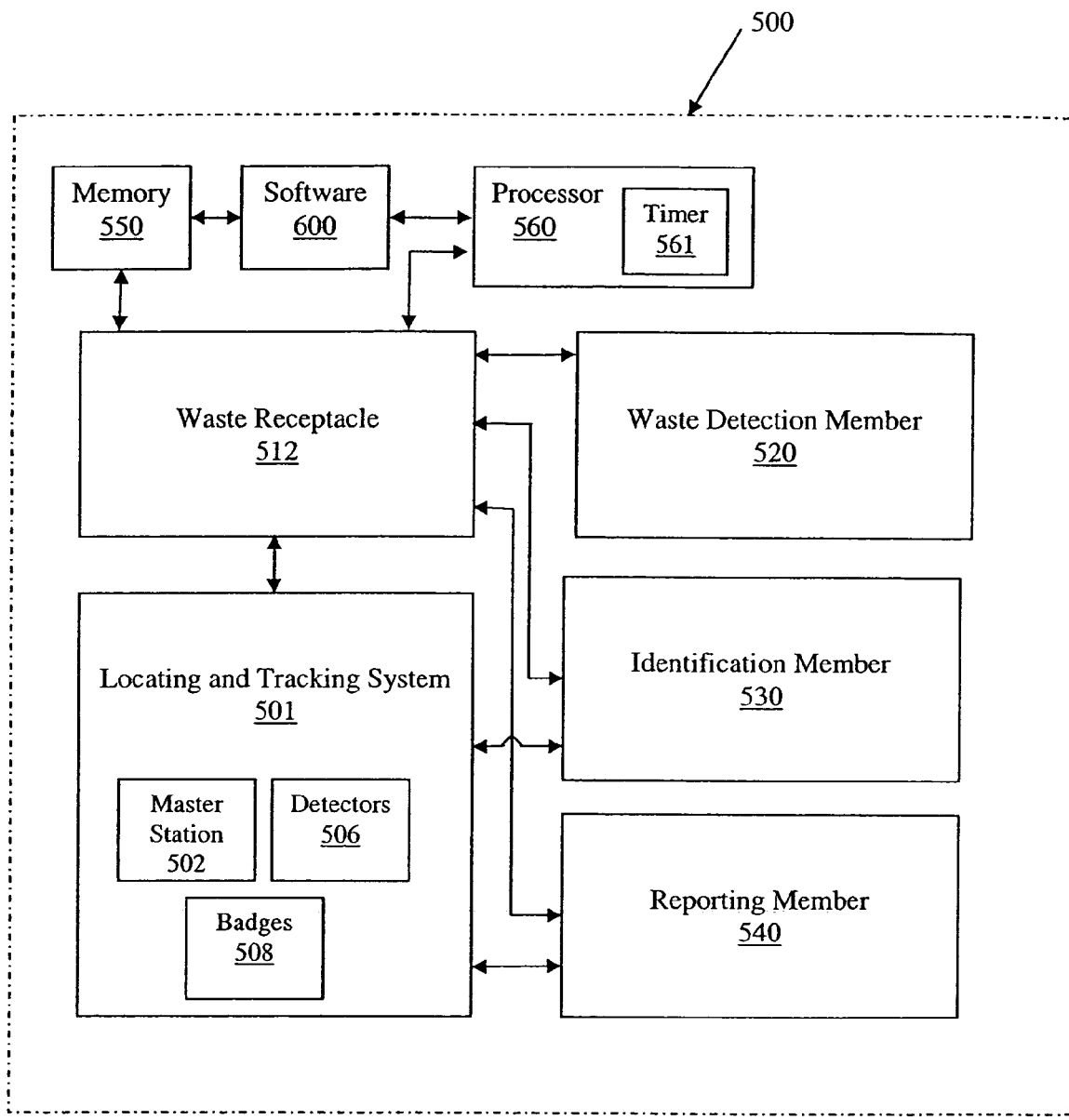
FIG. 10 is a diagrammatical block diagram illustrating the components of a second embodiment of the waste segregation compliance system of the present invention.

Referring further to FIG. 10, a block diagram is shown to illustrate the interaction between the components of the waste segregation compliance system 500. Waste segregation compliance system 500 is generally composed of a locating and tracking system 501, a waste receptacle 512, a waste detection member 520, an identification member 530, and a reporting member 540. As explained below, waste detection member 520, identification member 530 and reporting member 540 have similar functions to that of corresponding members 220, 230, 240 in waste segregation compliance system 200.

Figure 10A:
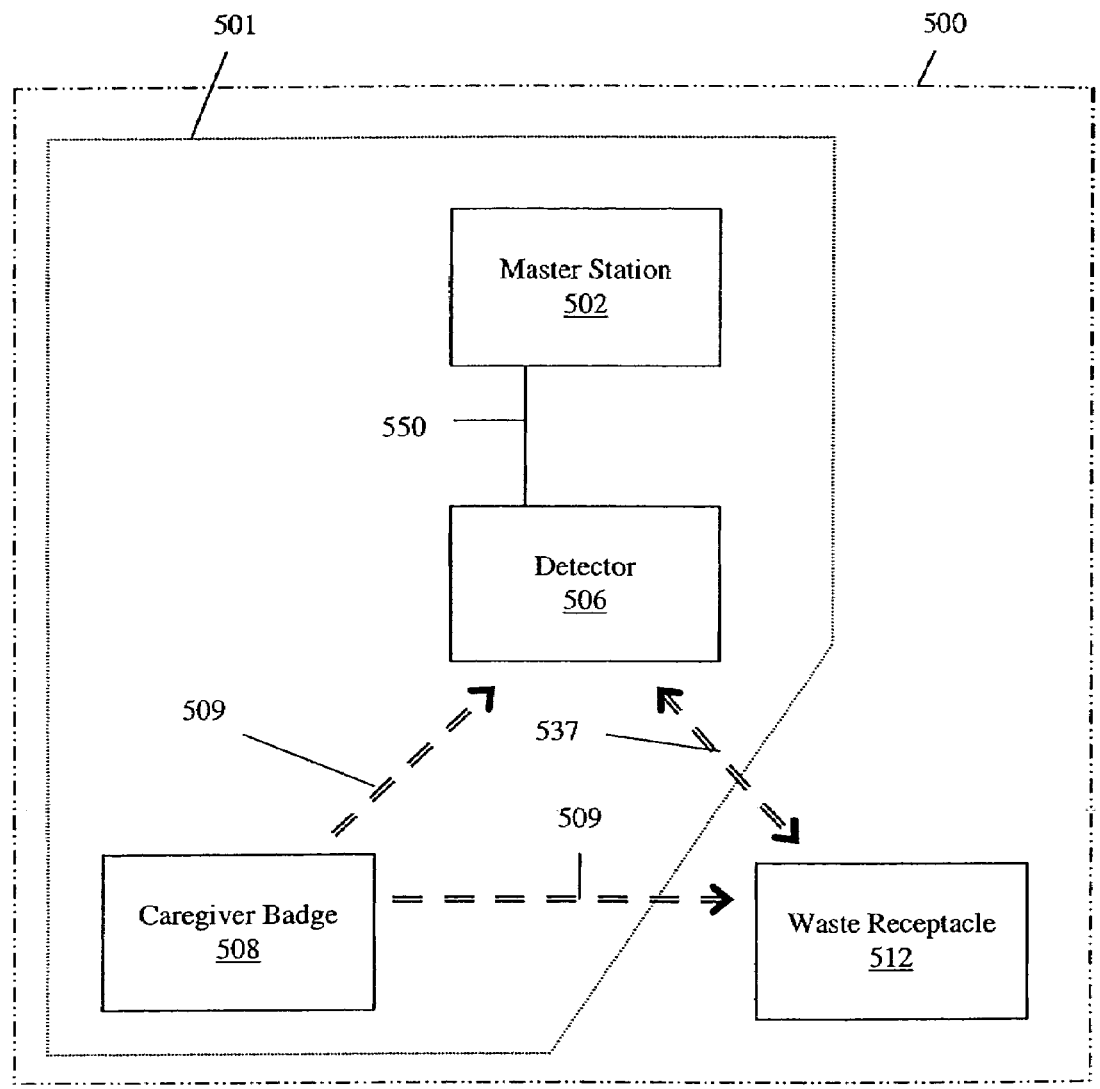
FIG. 10A is a diagrammatical block diagram illustrating an interaction between the waste receptacle of the waste segregation compliance system of FIG. 10 and the location tracking system of the waste segregation compliance system of FIG. 10.

As shown in FIGS. 10 and 10A, location and tracking system 501 includes master station 502 and a plurality of detectors 506 located in areas of the hospital, such as, for example, patient rooms 503. Master station 502 communicates with detectors 506 over a hard-wired connection 550 as shown, for example, in FIG. 10A. Connection 550 between master station 502 and detectors 506 allows for the reception and transmission of information therebetween.

Figure 10B:
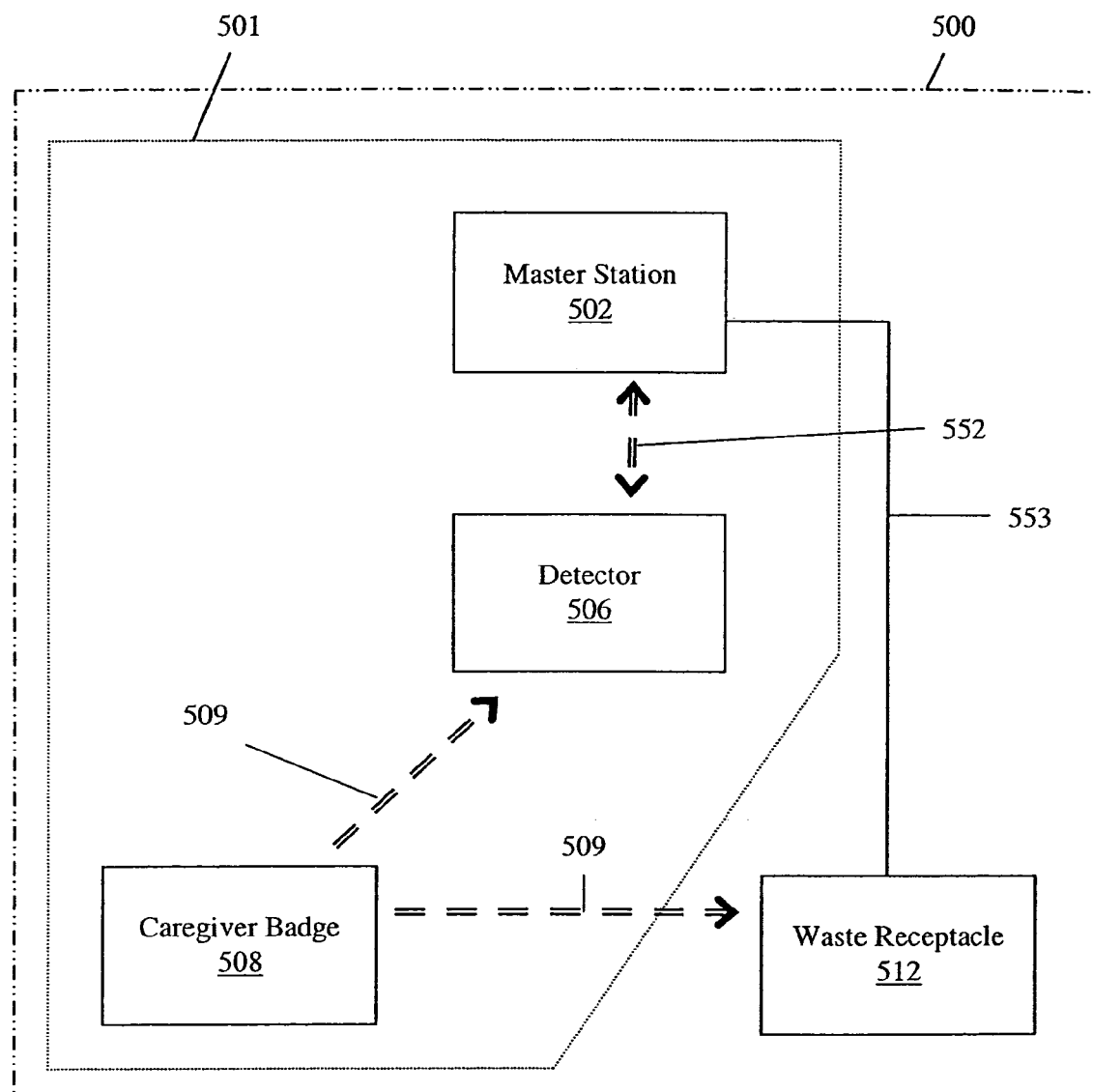
FIG. 10B is a diagrammatical block diagram illustrating an alternative interaction between the components of FIG. 10A.
Figure 10C:
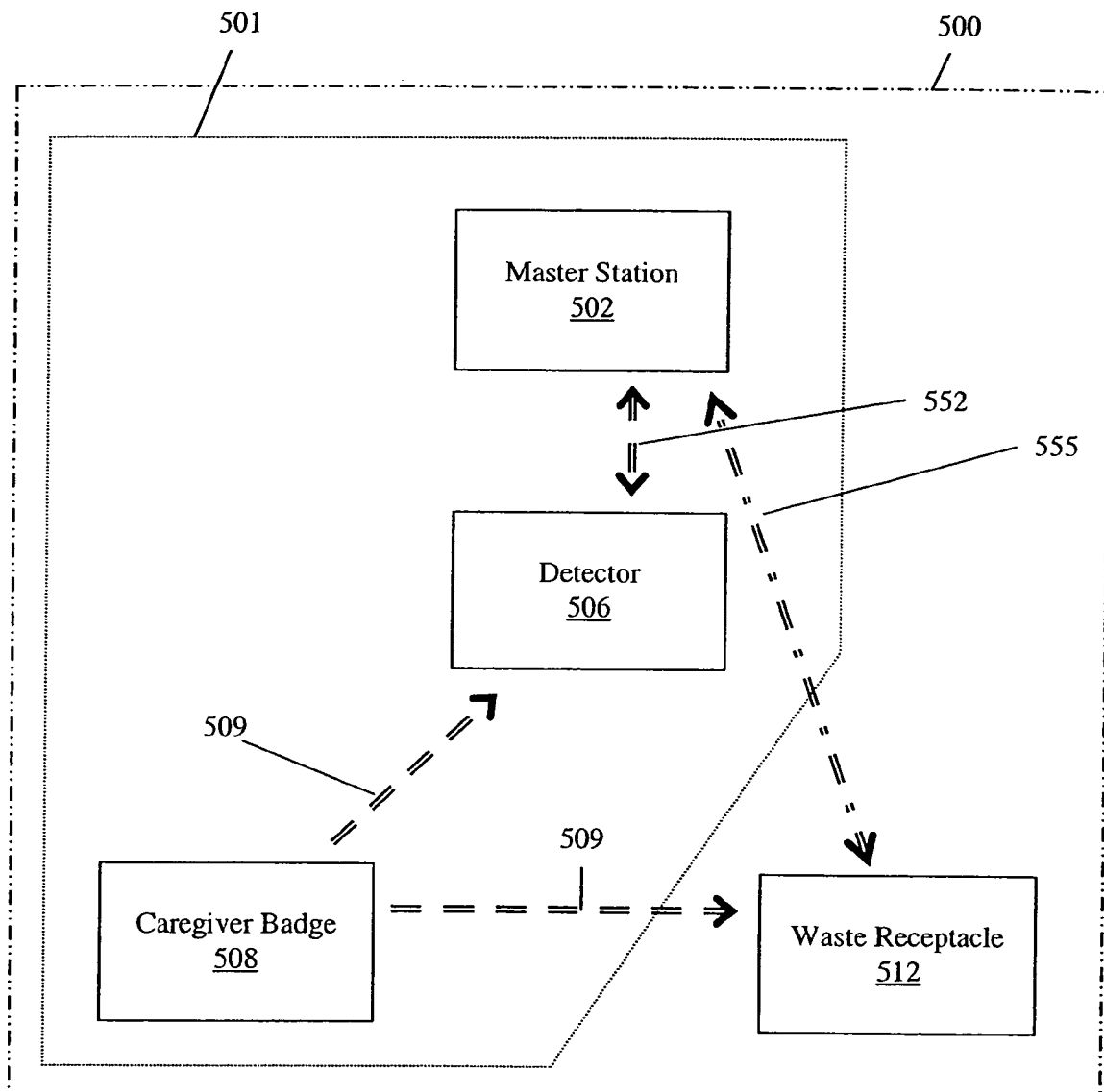
FIG. 10C is a diagrammatical block diagram illustrating an alternative interaction between the components of FIG. 10A.

In an alternative embodiment as shown in FIGS. 10B and 10C master station 502 and detector 506 communicate over a wireless connection 552. Connection 552 comprises a receiver positioned at either the master station 502 or at the detector 506, and a transmitter positioned at the other of the detector 506 and the master station 502. It should be appreciated that either the receiver or the transmitter may be replaced with a transceiver of the type known in the art. In one exemplary embodiment, detector 506 includes a transmitter which transmits a signal to a receiver at master station 502. Connection 552 in one exemplary embodiment is composed of bi-directional traffic, i.e. a receiver and transmitter (transceiver), at both the master station 502 and the detector 506. In an alternative embodiment, connection 552 is composed of unidirectional traffic, i.e. a receiver at one of the master station 502 and the detector 506, and a transmitter at the other of the detector 500 and the master station 502.

Figure 11:
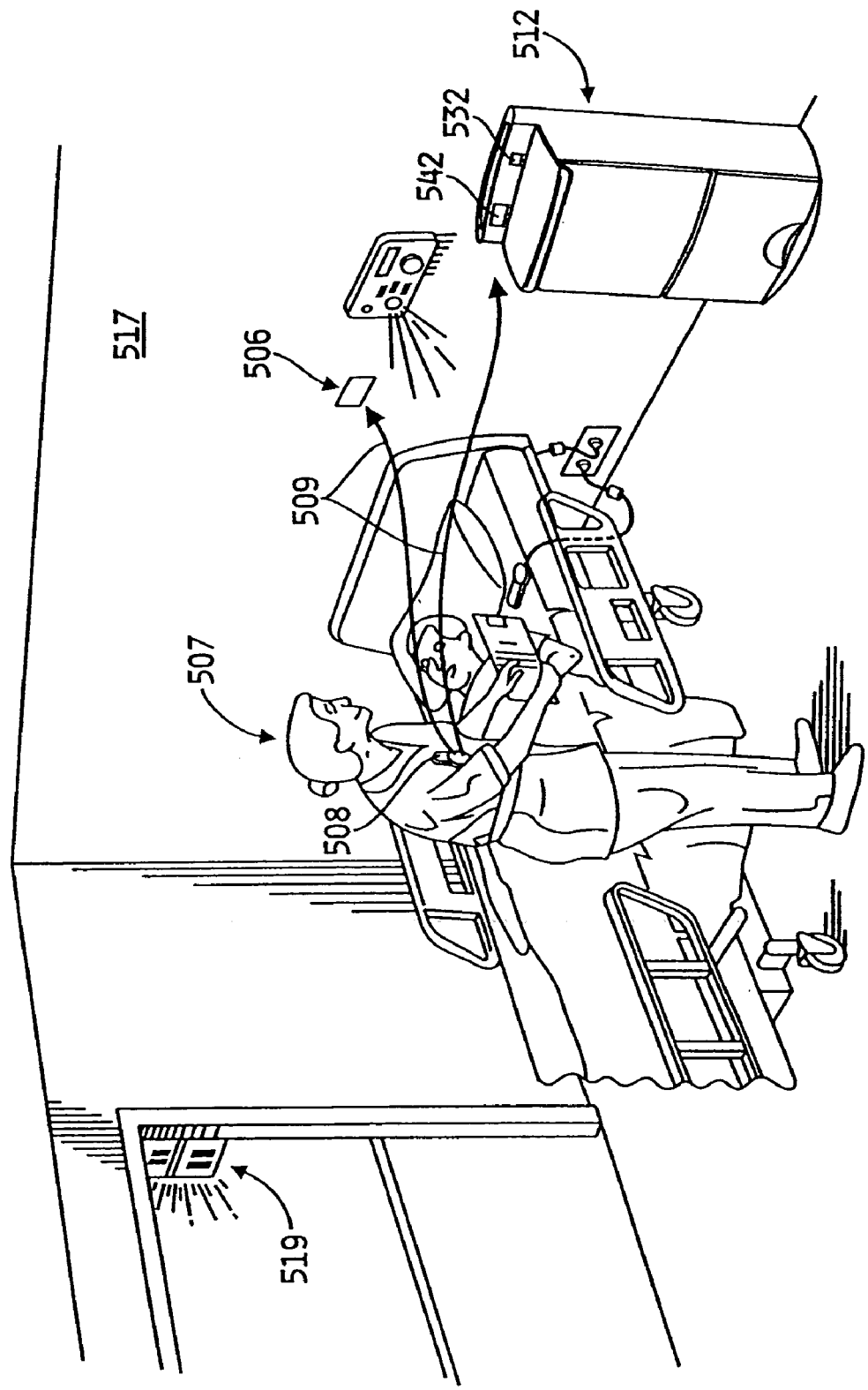
FIG. 11 is a perspective view of a waste receptacle of the present invention located in a patient's room.

Location and tracking system 501 further includes a plurality of badges 508, typically one of which is worn by each individual caregiver or person 507 as shown, for example, in FIG. 11. All detectors 506 and badges 508 include either a receiver, a transmitter or a transceiver. It should be appreciated that the detectors 506 and badges 508 may include any suitable conventional receiving members or transmitting members. An illustrative embodiment of badge 508 includes an infrared (IR) transmitter which transmits an identification signal 509, as shown in FIGS. 10A through 11, which may include, for example, a unique identification code specific to person 507 wearing badge 508. While the transmitter in each badge 508 may be an infrared (IR) transmitter, it is within the scope of the invention as presently perceived to include transmitters that convey any desired frequency of electromagnetic radiation, so long as the receivers in detectors 506 are compatible therewith and capable of detecting such transmissions. Detector 506 includes a receiver and detects a signal 509 transmitted by badge 508, converts signal 509 into an electronic message, such as a location signal 535, and forwards the message, or otherwise makes the message available to, master station 502. In this manner, the location of each person 507 is tracked as that person 507 moves throughout the facility. In one embodiment, the reception of signal 509 by detector 506 causes the performance of additional functions, such as deactivating a nurse call light 519 (FIG. 11).

Additional details concerning the structure and function of an exemplary caregiver locating and tracking system are disclosed in U.S. Pat. Nos. RE35,035, 5,561,412, 5,838,223, and 6,344,794, the disclosures of which are expressly incorporated by reference herein. Waste segregation system 500 is also capable of being incorporated into the hygiene monitoring system described in co-pending PCT Patent application Serial No. PCT/US00/29896, which is assigned to the assignee of the present invention, and is expressly incorporated by reference herein.

Referring further to FIGS. 10 through 11, waste segregation compliance system 500 includes waste receptacle 512 which interacts with caregiver locating and tracking system 501. As explained below in more detail, waste receptacle 512 monitors the amount and type of waste 504 deposited into at least one compartment 570, 580, 590 and the identity of the person 507 depositing the waste 504. Waste receptacle 512 through reporting member 540 conveys, or makes available, information to master station 502. In the embodiment of FIG. 10A, the information from waste receptacle 512 is made available to master station 502 through a wireless connection 537 between waste receptacle 512 and detector 506. Detector 506 and master station 502 interact as previously explained. Alternatively, waste receptacle 512 and master station 502 interact directly either over a hard wired connection 553 (FIG. 10B) or a wireless connection 555 (FIG. 10C).

Figure 13A:
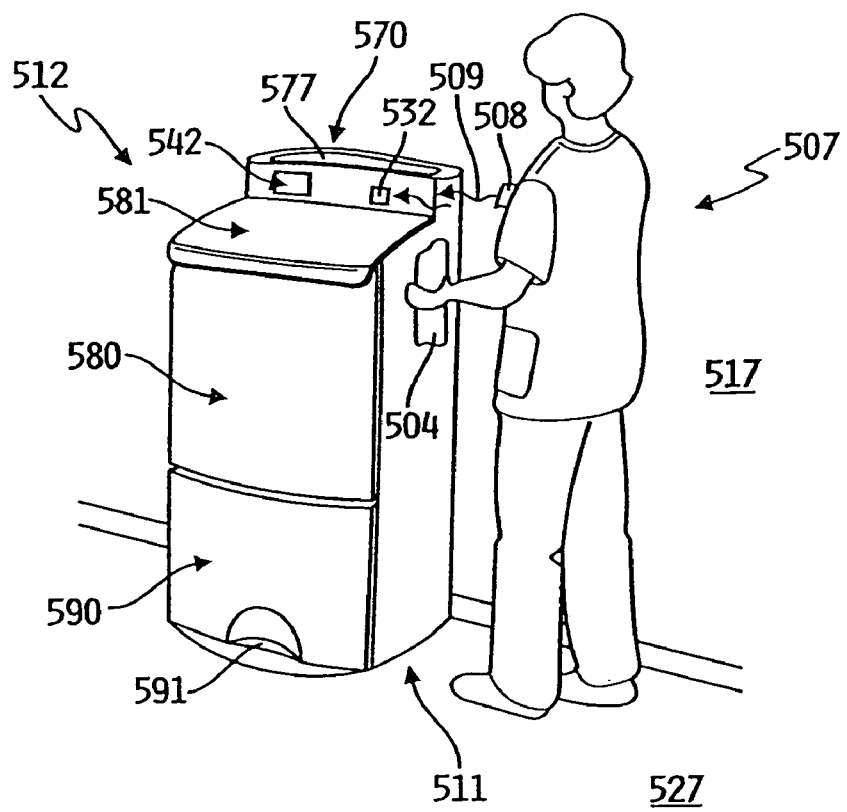
FIG. 13A is a perspective view of the waste receptacle of FIG. 12 for use by a caregiver.

As shown in FIGS. 11 and 13A, a person 507 approaches waste receptacle 512 with waste 504. Badge 508 is associated with person 507 for transmitting identification signal 509. Identification member 530 of waste segregation compliance system 500 includes a detector 532 to detect identification signal 509. It is well known in the art to determine an identification code from a received signal 509 which was originally transmitted with the identification code embedded therein. It is within the scope of the present invention for badge 508 to include a receiver, such that waste segregation compliance system 500 is able to poll or interrogate badge 508, thereby causing badge 508 to transmit identification signal 509.

Depending on the location of detector 506 relative to waste receptacle 512 and the range of the identification signal 509 transmitted by badge 508, detector 506 and detector 532 may be monitoring generally the same area of the healthcare facility. In such an instance, either detector 506 or detector 532 is redundant. In one exemplary embodiment, detector 506 is a part of identification member 530 and generates a location signal 535 in response to the reception of identification signal 509. Location signal 535 is made available to master station 502 over connection 550 or 552 (FIGS. 10A through 10C). Since detector 506 is generating location signal 535 for the region including waste receptacle 512, waste receptacle 512 does not require a separate detector 532. Master station 502 processes location signal 535 to determine and track the location of person 507. If master station 502 receives a deposit signal 525, then report signal 245 is generated based on the deposit signal 525 and the location signal 535 corresponding to the time frame of deposit signal 525.

In an alternate embodiment, equipment, files, disposable items, the packaging of disposable items, the packaging of consumables such as implants, waste as described above, etc. (hereinafter referred to as "item(s) 1204") are provided with an attached tag or transponder (hereinafter referred to as "tag(s)1208"). Tags 1208 may include data about item 1204, such as a unique item identifier, an item batch identifier, the cost, weight, or expiration date of item 1204, etc. Tags 1208 and the associated data gathering system described below may employ a variety of different technologies and incorporate any of the above-described waste segregation compliance systems 100, 200, 500 and/or locating and tracking system 501. For example, tags 1208 may include a transmitter similar to badges 508, such as an IR transmitter, and a memory, or use bar-code technology to store and convey the data.

Alternatively, tags 1208 may include an RFID device (either active or passive) for providing the data to a receiver as described below. Such RFID devices are produced, for example, by Intermec Technologies Corporation of Everett, Wash. RFID tags 1208 may be configured for read-only operation, volatile read/write operation, or write once/read many (WORM) operation. Such tags 1208 do not require contact or line-of-sight reading.

Figure 11A:
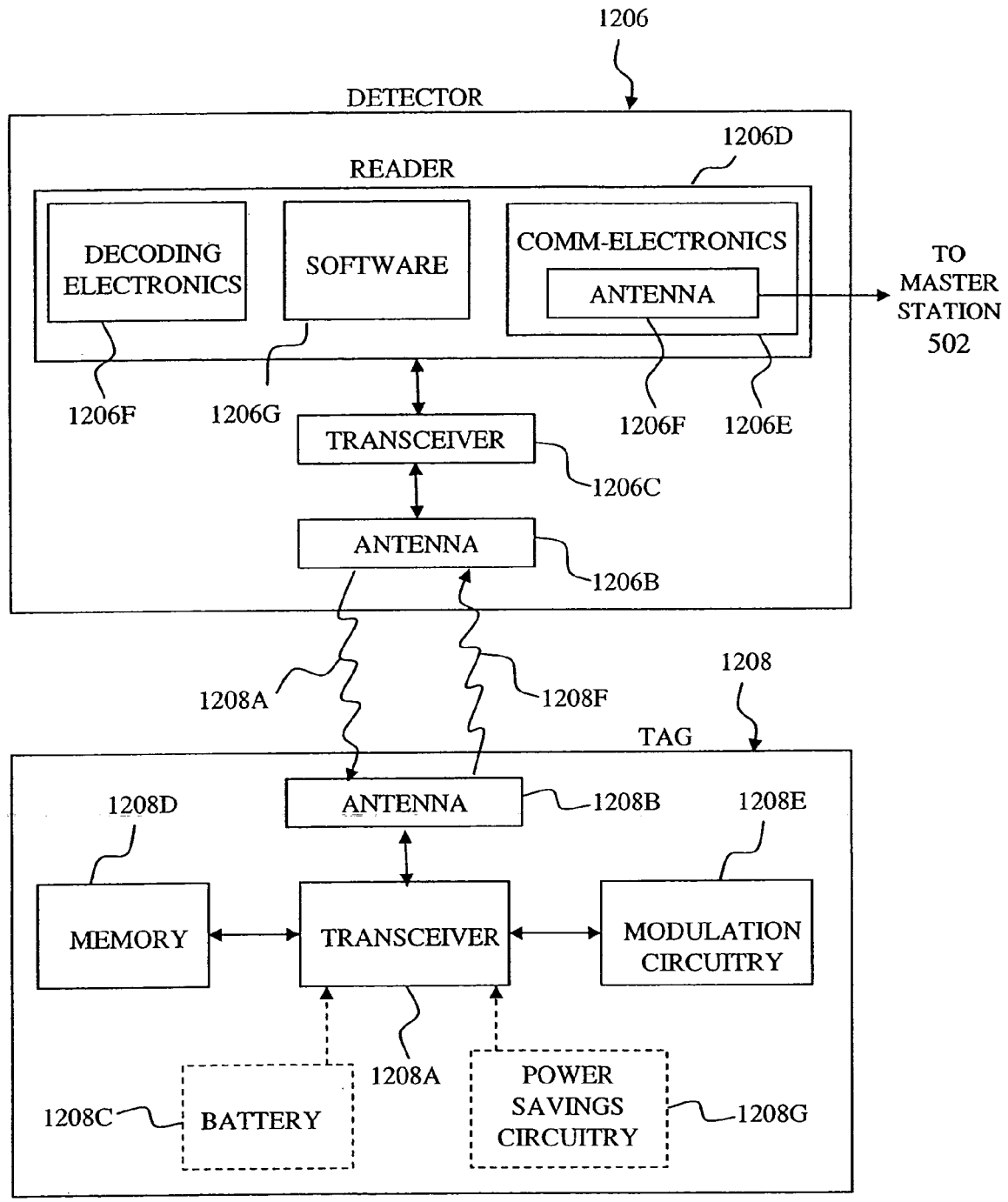
FIG. 11A is a block diagram of a RFID tag and a RFID detector.

As shown in FIG. 11A, active RFID tags 1208 may include a transmitter, and a receiver (or a transceiver 1208A), an antenna 1208B, and a battery 1208C to provide power to transceiver 1208A. Tag 1208 may further include a memory 1208D to store data relating to item 1204, and modulation circuitry 1208E to provide a tag signal 1208F conveying such information as further described below. In an alternate embodiment, active RFID tags 1208 may further include a conventional power savings circuit 1208G that interrupts or reduces the supply of power to the tag components when tag 1208 remains inactive (does not transmit or receive information) for a predetermined period of time. Tag 1208 remains in this power savings mode until it next receives a signal from a detector 1206 as further described below.

Passive RFID tags 1208 may include similar components. Typically, passive RFID tags 1208 reflect RF signals received from detectors 1206, and add information relating to item 1204. More specifically, when tag 1208 comes with range of a detector 1206, the tag's antenna 1208B receives an RF detector signal 1206A transmitted by detector 1206. Signal 1206A may also be used to provide power to tag 1208 as is well-known in the art. Thus, passive RFID tags 1208 may not include a battery 1208C. Battery 1208C may, however, be included in passive RFID tags 1208 to provide power to tag memory 1208D (if any), or modulation circuitry 1208E. After detector signal 1206A is received, tag modulation circuitry 1208E encodes a tag signal 1208F with the desired information (such as the unique item identifier, item batch number, etc.). Tag signal 1208F is then transmitted back to detector 1206 either via the same antenna 1208B that received detector signal 1206A, or another transmission antenna included on tag 1208.

Tags 1208 may be packaged in a variety of ways. For example, tags 1208 (including the transceiver, antenna, and any other components) may be enclosed within a container, case, or package adapted for attachment to an item 1204 or a person 1207 using adhesive, clips, or any other suitable attachment method. Alternatively, tags 1208 may be incorporated into a label for application (via adhesive or some other suitable attachment method) to an item 1204 or person 1207. Such labels may be printed using special printers, such as those produced by Zebra Technologies of Vernon Hills, Ill., that employ printing technology similar to that employed by conventional bar-code printers.

Detector 1206 for use with RFID tags 1208 generally includes an antenna 1206B, a transceiver 1206C, a reader 1206D, and communication electronics 1206E including antenna 1206F for wirelessly communicating with a central processing system, such as master station 502. Of course, communication electronics 1206E could alternatively be hardwired to master station 502. Transceivers 1206C transmit the RF energy of detector signal 1208A to activate passive tags 1208 (or active tags 1208 in power savings mode) and power the response transmission (tag signal 1208F) from passive tags 1208. Generally, transceiver 1206C is coupled to antenna 1206B and reader 1206D. Antenna 1206B generates an electrical field defining the range of detector 1206. As will be further described below, the antenna 1206B may be incorporated into a doorway of patient rooms 503, a pass-through wall of a facility, a waste receptacle, a cabinet, or a variety of other structural elements or pieces of equipment.

Detector reader 1206D controls the transmission of detector signals 1206A by transceiver 1206C and antenna 1206B, and receives and processes tag signals 1208F from tags 1208 as received by antenna 1206B and transceiver 1206C. Reader 1206D includes communication electronics 1206E, decoding electronics 1206F for decoding the information included in tag signals 1208F, and software 1206G. The decoded information is provided to communication electronics 1206E for transmission to, for example, master station 502. Software 1206G may implement anti-collision algorithms as are commonly known in the art to permit substantially simultaneous reception of multiple tag signals 1208F.

In one application of tags 1208 and detectors 1206, tags 1208 are attached to all incoming items 1204 at a location or locations outside the healthcare facility (e.g., when items 1204 are manufactured, packaged, shipped, etc.). As items 1204 are received at the healthcare facility, all items 1204 are passed through receiving ports or pass-through walls at the facility equipped with detectors 1206. As items 1204 are passed through the receiving ports, the data relating to items 1204 is read by detectors 1206 and transmitted to master station 502. Since detectors 1206 may implement anti-collision algorithms, tag signals 1208F from all items 1204 within containers of items 1204 may be received substantially simultaneously. Since no activity in addition to standard receiving activities is required in such an application, the data relating to the received items 1204 is collected "passively," without scanning, manually data entry, or otherwise "actively" collecting data. Accordingly, an inventory of all received items 1204 may automatically be maintained at master station 502.

By incorporating detectors 1206 at various locations throughout the healthcare facility (e.g., doorways to patient rooms 503, operating rooms, recovery rooms, entryways to particular areas of the facility, etc.), the location of items 1204 equipped with tags 1208 may be automatically tracked using locating and tracking system 501. Specifically, detectors 506 of system 501 may be replaced with detectors 1206, and badges may be replaced with tags 1208. As should be understood from the foregoing, people 507 may also be tracked using tags 1208 instead of badges 508. In this manner, the people 507 may be associated by location with items 1204, and the associated people 507 and items 1204 may be associated with events such as scheduled procedures, item 1204 disposal, etc.

For example, by employing business logic at master station 502, assumptions may be made regarding the activities of people 507 based on their proximity to items 1204. For example, if a person 507 enters a patient room 503 with an item 1204 such as suction canister having a tag 1208 on the packaging of the canister, the identity and location of the person 507 and the item 1204 may be ascertained by master station 502 via a detector 1206 in the doorway of patient room 503 according to the methods described above. The location of person 507 and item 1204 may be further pin-pointed by including additional detectors 1206 at various locations within patient room 503. For example, if a detector 1206 is located near the patient bed, master station 502 may properly assume that the suction canister 1204 is being used by person 507 to provide healthcare to the patient occupying the bed.

The waste segregation compliance systems 100, 200, 500 described above may be used to further verify the above-described assumption. For example, by equipping waste receptacles 110, 210, 510 with detectors 1206 (to carry out the functions of waste detection members 120, 220, 520 and identification members 130, 230, 530), master station 502 may determine the final disposition of item 1204. If person 507 deposits item 1204 into waste receptacle 110, 210, 510, then according to the methods described above, detector 1206 of waste receptacle 110, 210, 510 reports to master station 502 the fact that person 507 discarded item 1204 in waste receptacle 110, 210, 510. Consequently, master station 502 may remove item 1204 from the facility inventory, and record the fact that person 507 disposed of item 1204.

Moreover, since tag 1208 of item 1204 includes data relating to item 1204, the decoded signal sent to master station 502 from detector 1206 may include a description of item 1204. Of course, the unique item identifier included in tag signal 1208F may alternatively be associated with an item description. In either case, master station 502 may determine that item 1204 is a suction canister. Accordingly, the bill for the patient in room 503 may be adjusted to include the cost of a suction canister. Additionally, since detector 1206 may be located adjacent any one of compartments 270, 280, 290 of, for example, waste receptacle 210 to report the deposit of items 1204 in a specific compartment 270, 280, 290, master station 502 may determine whether item 1204 was deposited in the correct compartment 270, 280, 290. In this example, item 1204 (a suction canister) would be classified as IMW. Thus, master station 502 may generate a report as described above indicating whether person 507 deposited item 1204 in a compartment 270, 280, 290 designated to receive IMW in compliance with an established waste segregation policy.

It should be understood from the foregoing that, in an alternate embodiment, a single detector 1206 could be located at waste receptacle 210 to function in cooperation with waste detection member 220. In such an embodiment, detector 1206 receives tag signals 1208F from tags 1208 associated with person 507 and item 1204 when person 507 and item 1204 come with the range of detector 1206. When person 507 deposits item 1204 into a particular compartment 270, 280, 290, waste detection member 220 generates deposit signal 225 based on input from threshold components 274, 276, sensor 296, or a sensor associated with compartment 290 as described above. Accordingly, detector 1206 provides master station 502 an identification of person 507 and item 1204, and deposit signal provides an indication of which of compartments 270, 280, 290 received item 1204.

Figure 12:
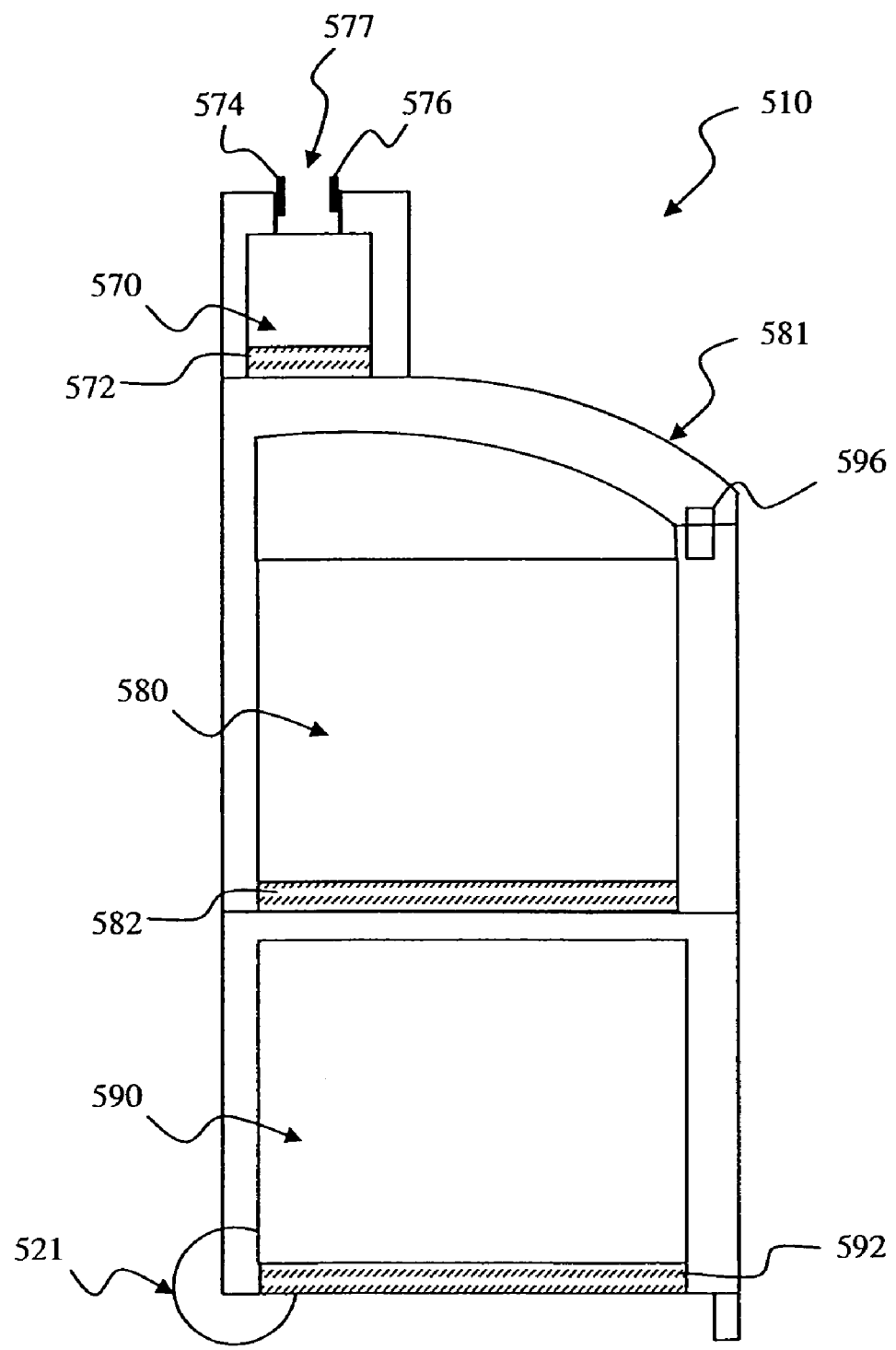
FIG. 12 is a diagrammatical, side view of a waste receptacle of the present invention.
Figure 13B:
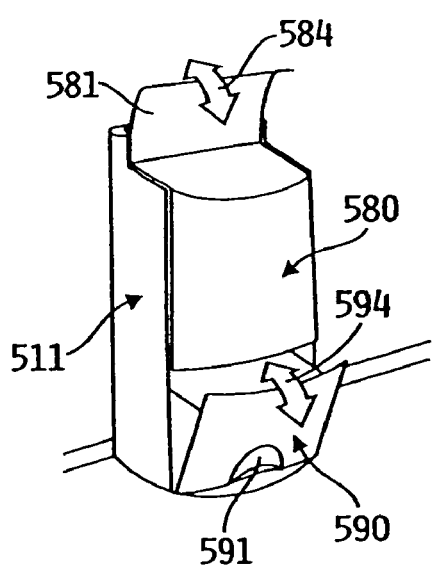
FIG. 13B is a perspective view of the waste receptacle of FIG. 13A, illustrating the operation of the waste receptacle.
Figure 13C:
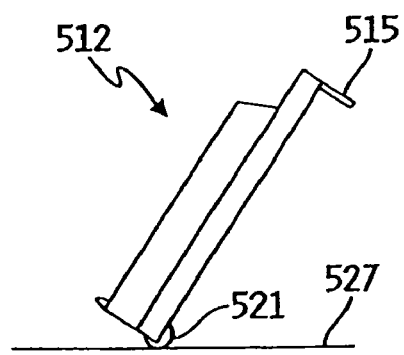
FIG. 13C is a side view of the waste receptacle of FIG. 13A.

Waste receptacle 512, as shown in FIGS. 12 through 13C, includes a housing 511 having separate compartments 570, 580, and 590. By having multiple compartments 570, 580, and 590, different types of waste 504 can be segregated based upon waste type. In an exemplary embodiment, compartment 570 is designated for sharps waste such as needles, compartment 590 is designated for infectious medical waste (IMW) such as soiled surgical dressings and syringes, and compartment 580 is designated for general waste, such as any waste not designated for compartments 570 or 590. It is not a requirement that compartments 570, 580, and 590 are contained within a single housing 511. For example, in one embodiment compartment 570 may be supported by a wall 517 and compartments 580 and 590 are located within a floor receptacle.

It is within the scope of the present invention to assign different types of waste 504 to compartments 570, 580 and 590, and to vary the number of compartments. For example, in one embodiment waste receptacle 512 is composed of a single compartment. A single compartment arrangement is advantageous when only a single type of waste 504 is to be tracked. Only a single type of waste 504 requires tracking when disposal costs are generally uniform for different types of waste 504 except for one type of waste which has a disposed cost substantially different from that of other types of waste.

Referring to FIGS. 12 and 13A, waste 504 is placed into compartment 570 by passing waste 504 through an opening 577. Waste 504 is placed into compartment 580 by lifting covering 581, as shown in FIG. 13B by arrow 584. Waste 204 is placed in compartment 590 by applying pressure to a foot pedal 591 which causes compartment 590 to tilt forward, as indicated by arrow 594 in FIG. 13B and in the same manner as described above with respect to FIG. 4B.

Referring to FIG. 13C, waste receptacle 512 further includes a handle 515 and wheels 521. Wheels 521 are supported at a lower rear end of housing 511. Handle 515 is located at an upper rear end of housing 511 and extends outwardly therefrom. In one embodiment, handle 515 is pivotally mounted for storage within a recess (not shown) of housing 511 when waste receptacle 512 is in use. Handle 515 and wheels 521 allow for the easy transport of waste receptacle 512 from location to location. Waste receptacle 512 is moved, similar to a two-wheel cart, by tilting housing 511 backwards about wheels 521, such that only wheels 521 are contacting the floor 527. The waste receptacle 512 may then be rolled either forward or backward on wheels 521.

The mobility of waste receptacle 512 allows for waste receptacle 512 to be moved to a conventional central disposal location where compartments 570, 580 and 590 are emptied into corresponding larger compartments. Alternatively, the mobility of waste receptacle 512 allows person 507 to take waste receptacle 512 with them during their work shift.

Waste detection member 520 detects when waste 504 is deposited in one of or a combination of compartments 570, 580 and 590. Waste detection member 520 generates a deposit signal 525 in response to the detection of a use of waste receptacle 512. Compartments 570, 580, and 590, preferably contain sensors, such as scales 572, 582, and 592, to detect a change in the weight of the respective compartment 570, 580, 590. In one exemplary embodiment, waste detection member 220 determines the compartment 570, 580 or 590 into which waste 504 was deposited by determining the change in weight for each compartment 570, 580, 590.

In another exemplary embodiment, waste detection member 520 includes two components 574 and 576 associated with compartment 570 and intended to replace or augment sensor 572. Components 574 and 576 are designed to determine when waste 504 passes into opening 577. In one embodiment, component 574 is an emitter and component 576 is a detector configured to detect energy emitted by component 574. When waste 504 passes between emitter 574 and detector 576, the signal detected by detector 576 from emitter 574 is modified, indicating that waste 504 is being placed into compartment 570.

In a further alternative embodiment, waste detection member 520 includes a sensor 596 associated with covering 581, such that the sensor 596 identifies the deposit of waste 504 into compartment 580 by the opening of covering 581. Examples of a sensor to detect the opening of cover 581 may include an optical sensor, an inductive based sensor or a continuity sensor.

In a further alternative embodiment, waste detection member 520 includes a sensor to detect the level or volume of the waste in a compartment. Such level or volume sensors are known in the art and are especially tailored for use with applications which include liquid waste. An advantage of sensors 572, 582, and 592 over threshold components 574, 576 and sensors associated with the opening of cover 581, is that sensors 572, 582, and 592 detect not only the deposit of waste 504 into compartment 570, 580 and 590, but additionally the weight of waste 504. As such, the sensors 522, 582, 592 detect the deposit of waste and the quantity of waste deposited.

Referring now to FIGS. 11, 13A, 14, and 15, reporting member 540 includes a display screen 542. When waste compliance system 500 detects the deposit of waste 504 into compartment 570, 580 or 590 of waste receptacle 512 and identifies the person 507 adjacent waste receptacle 512, reporting member 540 reports the results of the detections. Generally, waste detection member 520 generates deposit signal 525 and identification member 530 generates location signal 535. Deposit signal 525 and location signal 535 are combined to generate report signal 545 which is made available to reporting member 540. In an alternative embodiment, reporting signal 545 includes location signal 535 even in the absence of a deposit signal 225, when the location of person 507 is being tracked independent of whether waste 204 was deposited in waste receptacle 512.

Figure 17:
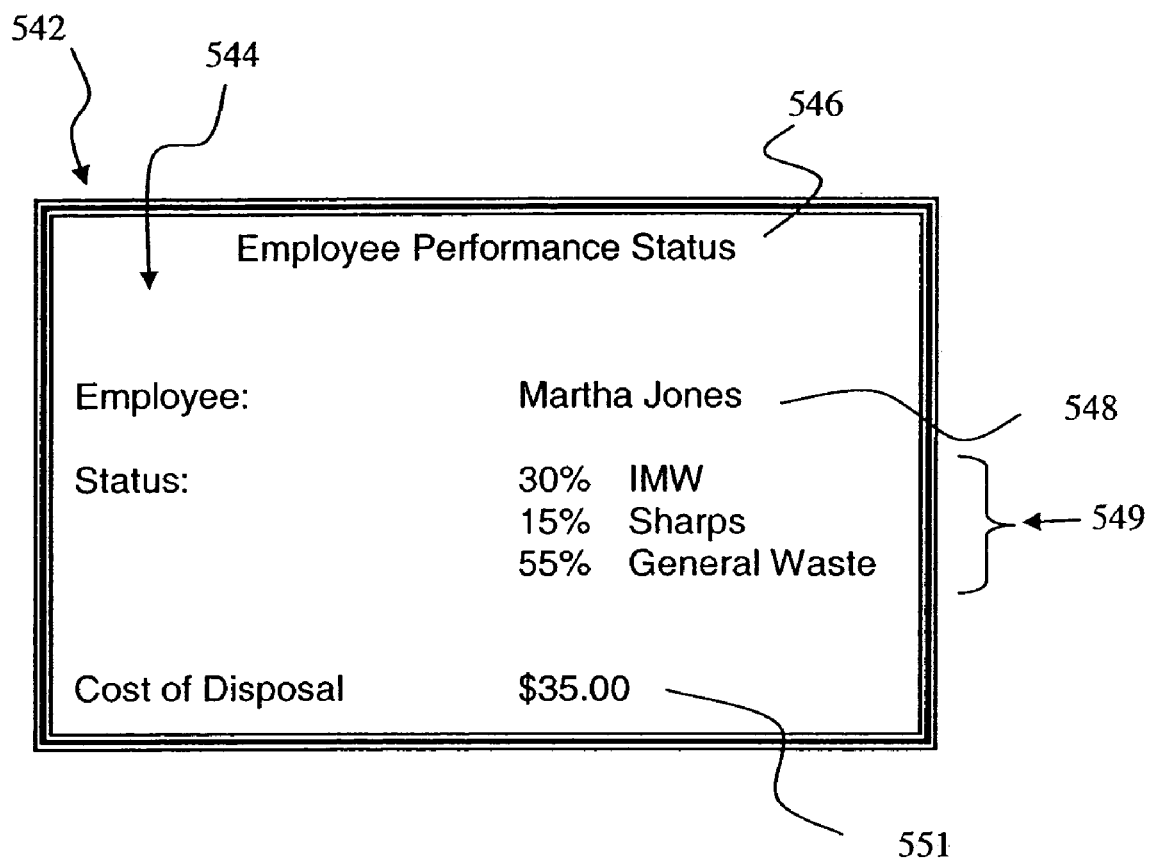
FIG. 17 is a sample waste segregation display report.

In FIG. 17, an illustrative report 544 is shown on display 542. Report 544 includes a title 546, a name or other identification 548 of person 507, a breakdown 549 of the waste 504 deposited and a calculated disposal cost 551.

In one exemplary embodiment, report signal 545 is generated at master station 502 from the receipt of location signal 535 and deposit signal 525. Report signal 545 is used to create various reports and to populate database files.

Figure 14:
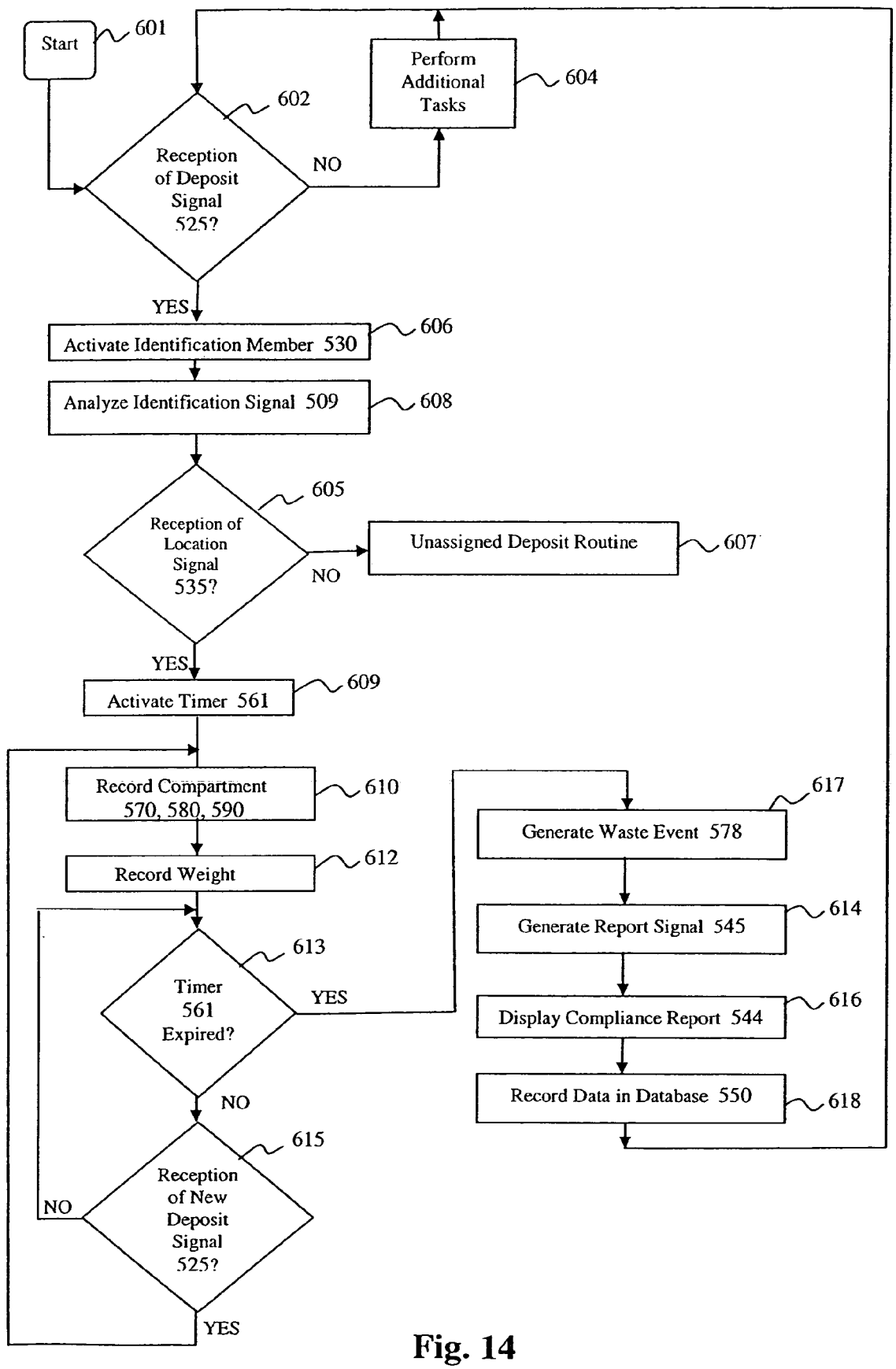
FIG. 14 is a flowchart representation of the steps performed by a first component of the software of the waste segregation compliance system of FIG. 10.
Figure 15:
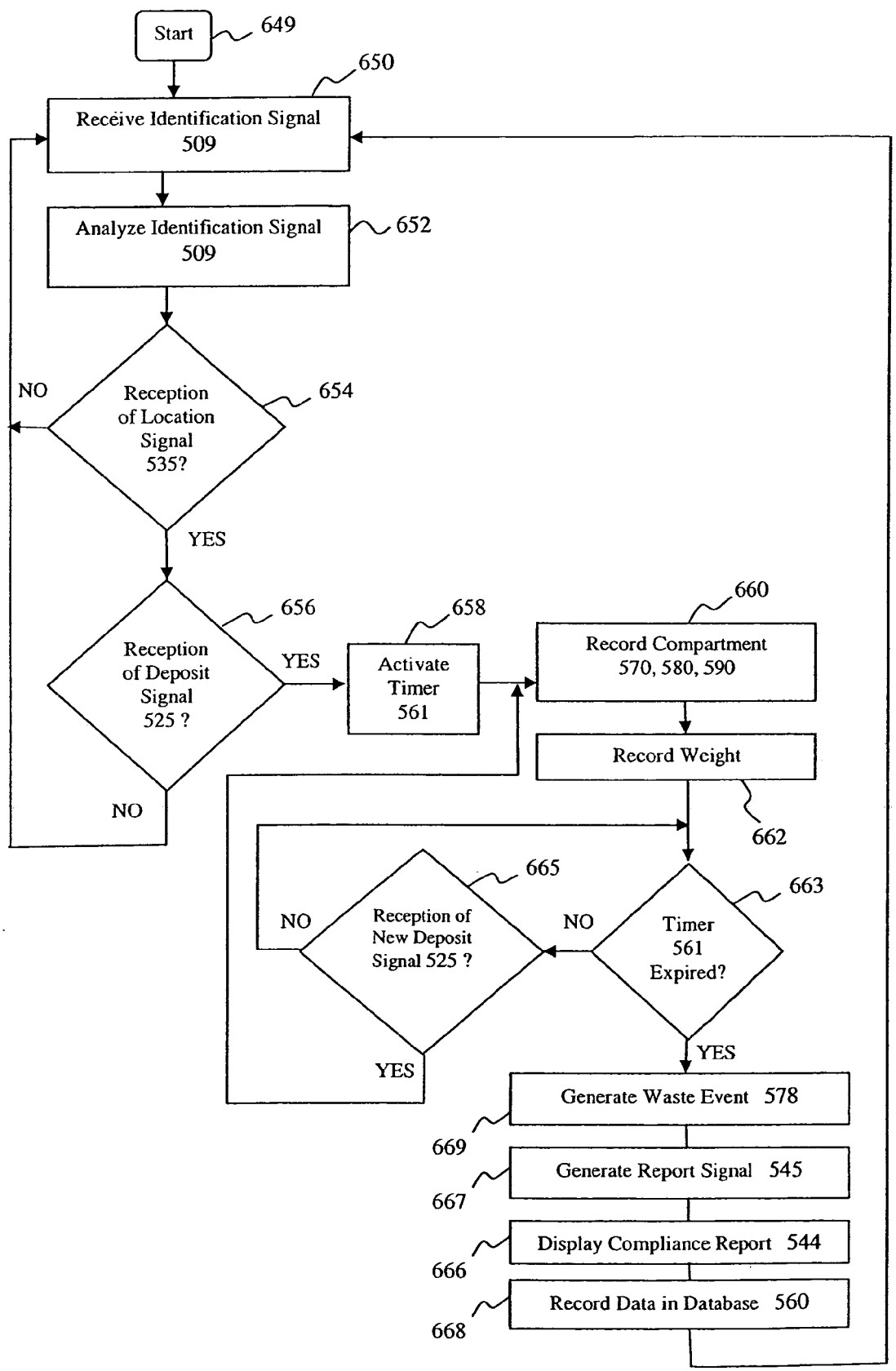
FIG. 15 is a flowchart representation of the steps performed by a second component of the software of the waste segregation compliance system of FIG. 10.

The operation of waste detection member 520, identification member 530 and reporting member 540 is controlled by processor 560 which executes software 600. Flowcharts corresponding to two components of software 600 executed by processor 560 are shown in FIGS. 14 and 15. In one embodiment, processor 560 is located at waste receptacle 512. In another embodiment, processor 560 is located at master station 502. In yet another embodiment processor 560 is representative of a collection of processors, some residing at waste receptacle 512 and others residing at master station 502, wherein the individual processors collectively perform the functions of software 600.

Figure 16:
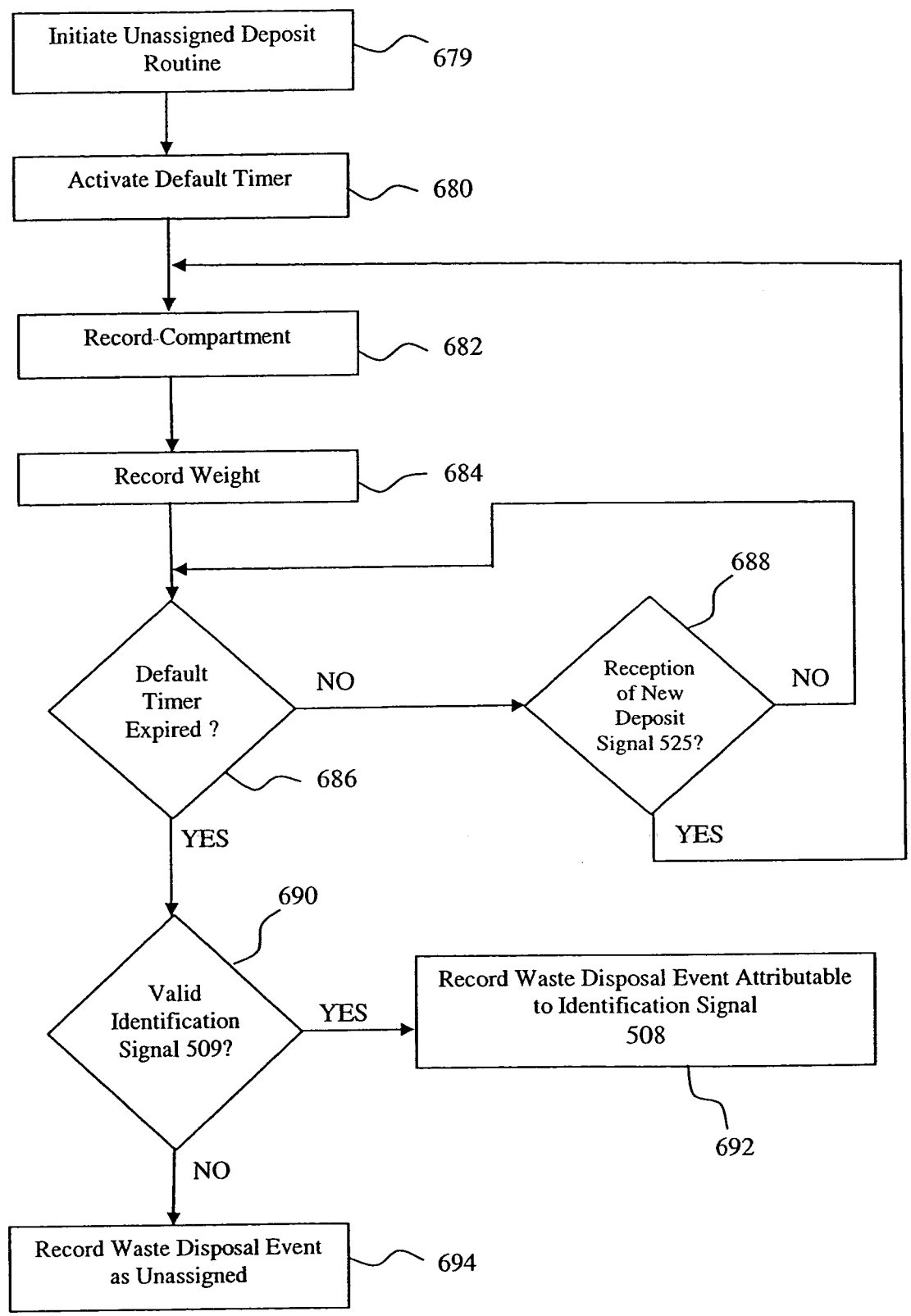
FIG. 16 is a flowchart representation of the steps performed by the software of the waste segregation compliance system of FIG. 10 in the absence of receiving a valid identification signal.

The first component of software 600 is executed when a deposit signal 525 is generated within a reasonable time prior to a location signal 535. The second component of software 600 is executed when a location signal 535 is generated within a reasonable time prior to a deposit signal 525. Each component is detailed below. Additionally, FIG. 16 illustrates the steps taken by software 600 when a valid identification signal 509 is not received by identification member 530 and hence a location signal 535 is not generated within a reasonable time after the reception of a deposit signal 525. The length of time corresponding to a reasonable time is a predetermined value of a variable within software 500. In one embodiment, a reasonable time is established to be equal to 1 second.

A flowchart illustrating the steps or functions performed by the first component of software 600 is shown in FIG. 14. Once the system 500 is activated at block 601, all variables are initialized or set to initial values. More particularly, the amount, typically the weight, of waste 504 in each compartment 570, 580, 590 is measured and stored in memory 560. Software 600 waits to receive deposit signal 525 from waste detection member 520, as represented at block 602. As detailed above, deposit signal 525 represents the detection of waste 504. In an exemplary embodiment, software 600 is capable of performing additional tasks in the absence of the reception of deposit signal 525, as represented by block 604. For example, the additional tasks are initiated by an interrupt to the software execution. One example of an additional task, is the processing of location signal 535 in the absence of deposit signal 525 (see FIG. 15). If deposit signal 525 is received, then software 600 activates identification member 530.

Block 606 represents the activation of identification member 530 in response to waste 504 being detected by waste detection member 520. As detailed above, waste receptacle detector 532 detects the identification signal 509 emitted by badge 508. The received identification signal 509 is analyzed to determine the identity of person 507 at process block 608. If identification signal 509 is valid, then identification member 530 generates a location signal 535. If identification signal 509 is not valid, then identification member 530 does not generate a location signal 535. In an alternative embodiment, identification member 530 is continuously active such that location signal 535 is generated independent of the generation of deposit signal 525. For example, when detector 506 is part of identification member 530, identification member 530 is always activated because detector 506 is used to track and locate person 507 independent of whether person 507 deposits waste 504 within receptacle 512.

Software 600 checks to determine if a valid location signal 535 has been produced by identification member 530, as represented at decision block 605. If a location signal 535 has not been received, then software 600 initiates an unassigned deposit routine, as represented at process block 607. The unassigned deposit routine is explained in detail below in connection with FIG. 16. If a valid location signal 535 is received, software 600 activates timer 561 at block 609. The timer 561 controls the time frame wherein multiple deposits of waste 604 are all included in a single waste event 578 and attributed to the same person 507 identified in location signal 535. Waste event 578 includes all of the deposit signals 525 received during the period of time defined by the timer 561. By setting the timer 561 to a low or zero value, each deposit of waste 504 is recorded as a separate waste event 578. By increasing the timer 561 to a higher value multiple deposit signals 525 are included in the same event 578. The compartment 570, 580, 590 corresponding to the detected deposit signal 525 is recorded, as illustrated by block 610, and the weight of the contents of identified compartment 570, 580, 590 is recorded, as illustrated by block 612.

As detailed with respect to the previous embodiment, the current recorded weight of waste 504 within any compartment 570, 580 and 590 is a composite value of previously deposited waste 504. The software 600 is therefore capable of calculating the incremental change in weight due to the addition of new waste 504 into a respective compartment 570, 580 and 590. More particularly, the memory 550 stores a value for weight of waste 504 at a given time. After additional waste 504 is added to the respective compartment 570, 580 and 590, the processor 560, as instructed by software 600, determines a differential between the new weight of the compartment 570, 580 and 590 and the weight stored in memory 550. As such, the weight of the new additional waste 504 is efficiently calculated.

Software 600 determines if the timer 561 has expired at block 613. If the timer 561 has not expired, then at block 615 software 600 determines if an additional deposit signal 525 has been generated by waste detection member 520. If an additional deposit signal 525 has been received, then the process returns to block 610 where the compartment 570, 580, 590 corresponding to the deposit signal 525 is recorded. The weight of the compartment 570, 580, 590 is again recorded at block 612.

In another exemplary embodiment, software 600 records the weight of each compartment 570, 580, 590 only after the timer 561 has expired. As such, the total weight of waste 504, corresponding to the deposit signals 525, is recorded after the timer 561 has expired. In such a system, deposit signal 525 serves only as an indication of which compartments 570, 580, 590 are to be weighed.

Once the timer 561 has expired, as determined at decision block 613, software 600 generates waste event 578 as indicated in block 617. Waste event 578 is a summary of all deposit signals 525 received prior to the expiration of the timer 561 and includes the compartment 570, 580 and 590 into which waste was deposited and the amount of waste deposited. Report signal 545 is generated by software 600 and sent to reporting member 540 at block 614. Report signal 545 includes information from location signal 535 and waste event 578.

Reporting member 540 communicates compliance report 544 which was created from report signal 545. In one exemplary embodiment, compliance report 544 is displayed on display 542 as illustrated at block 616. In another exemplary embodiment, a tangible or hard copy of compliance report 544 is created with an appropriate output device, such as a printer (not shown). In yet another exemplary embodiment, the data comprising compliance report 544 is made available in an electronic format to a database or e-mail system, such that the data can be provided to personnel or other software programs.

An example compliance report 544 is shown in FIG. 17. Compliance report 544 illustratively includes title 546, name or other identification 548 of person 507; waste breakdown 549 and disposal cost 551. The percentage of the overall waste 504 deposited in each compartment, 570, 580, 590 is included in waste breakdown 549. The disposal cost is figured by multiplying the weight of each type of waste deposited by the average unit cost for disposing of that type of waste 504. The disposal costs for each type of waste 504 are then added together to provide an overall disposal cost. The average unit disposal costs for each type of waste 504 are variable values stored in memory 550 and accessed by software 600. Alternatively, compliance report 544 does not include disposal cost 551. The data detected is stored in a database or other file memory 550, as illustrated at block 618. In one exemplary embodiment, report signal 545 is stored in memory 550, along with the weight of each compartment 570, 580 and 590.

The timer 561 of blocks 609 and 613 of FIG. 14 provides person 507 with a fixed duration of time before software 600 records waste disposal event 578. If the span of time between two or more deposits of waste 504, and the corresponding reception of two or more deposit signals 525, are within the fixed duration of time set by the timer 561 then a single corresponding waste disposal event 578 is recorded when the timer 561 expires. If the span of time between any two time adjacent deposits of waste 504 and corresponding deposit signals 525 exceeds the fixed duration of time set by timer 261, then two waste disposal events 578 are recorded, one for each deposit.

In another exemplary embodiment, instead of the timer, software 600 determines whether person 507 is still detected by detector 532 to set the time frame of waste event 578 thereby eliminating the need for timer 561. If identification signal 509 is still being received by detector 532, software 600 continues to monitor and record compartments 570, 580, 590 and weights of waste 504. Once identification signal 509 is no longer received by detector 532, software 600 generates waste event 578 and generates report signal 545.

A flowchart illustrating the steps or functions performed by the second component of software 600 is shown in FIG. 15. After activation of the system 500 at block 649 all variables are initialized or set to initial values. More, particularly, the amount, typically the weight, of waste 504 in each compartment 570, 580, 590 is measured and stored in memory 550. An identification signal 509 is received by identification member 530 at block 650. More particularly, detector 532 detects the presence of person 507 by receiving identification signal 509. The identification signal 509 is next analyzed at process block 652. If identification signal 509 is valid, then identification member 530 generates a location signal 535. If identification signal 509 is not valid, then identification member 530 does not generate a location signal 535.

The software 600 at decision block 654 determines whether processor 560 has received location signal 535 from identification member 530. If the location signal 535 has been received by processor 560, then the software 600 continues at decision block 656, otherwise the process returns to block 650. At block 656 software 600 determines if waste detection member 520 has generated a deposit signal 525. If waste 504 has not been detected, software 600 loops back to block 650 and waits for the reception of a second, in time but not necessarily unique, location signal 535.

If a deposit signal 525 is received at block 656, software 600 activates timer 561 at block 658. Next, the software 600 records within memory 550 the compartment 570, 580, 590 corresponding to deposit signal 525 at block 660, and determines and records within memory 550 the weight of the contents of the identified compartment 570, 580, 590 at block 662.

Software 600 determines if the timer 561 has expired at decision block 663. If the timer 561 has not expired, then software 600 determines if an additional deposit signal 525 has been generated by waste detection member 520 at decision block 665. If an additional deposit signal 525 has been received by processor 560, then the process returns to block 660. The compartment 570, 580, 590 corresponding to the deposit signal 525 and the weight of respective compartments 570, 580, 590 are recorded, as represented by blocks 660 and 662.

In another exemplary embodiment, software 600 records the weight of each compartment 570, 580, 590 only after the timer 561 has expired. As such, the total weight of waste 504, corresponding to the received deposit signals 525, is recorded after the timer 561 has expired. In such a configuration, deposit signal 525 serves only as an indication of which compartment 570, 580, 590 is to be weighed.

Once the timer 561 has expired, as determined at block 663, software 600 generates waste event 278 at process block 669. Waste event 578 is a summary of all deposit signals 525 received prior to the expiration of the timer 561 and includes the compartment 570, 580 and 590 into which waste was deposited and the amount of waste 504 deposited. Software 600 next instructs the processor 560 to generate and transmit report signal 545 to reporting member 540, as illustrated by block 667. Report signal 545 includes information from location signal 535 and waste event 578. The timer 561 illustrated in FIG. 15 provides person 507 with a fixed duration of time before software 600 records a waste disposal event 578.

In an alternative embodiment, software 600 determines whether identification signal 509 is still being received by detector 532 or detector 506 to set the time frame of waste event 578 thereby eliminating the need for timer 561. If identification signal 509 is still being received by detector 532, software 600 continues to monitor and record compartments 570, 580, 590 and weights of waste 504. Once identification signal 509 is no longer received by detector 532, software 600 generates waste disposal event 578.

Reporting member 540 communicates compliance report 544 which was created from report signal 545. In one exemplary embodiment, at block 666 compliance report 544 is displayed on display 542. In another exemplary embodiment, a tangible or hard copy report of compliance report 644 is created with an appropriate output device, such as a printer (not shown). In yet another exemplary embodiment, the data comprising compliance report 544 is made available in an electronic format to a database or e-mail system, such that the data can be provided to personnel or other software programs. An example of the compliance report 544 is described in detail above in connection with FIG. 17. The detected data is then stored in a database or file of memory 550, as illustrated at block 668. In an exemplary embodiment, the data stored in memory 550 includes the weight of compartments 570, 580, 590 and report signal 545.

FIG. 16 illustrates the unassigned deposit routine, which records a waste event 578 in the absence of the reception of a location signal 535. The unassigned deposit routine is initiated at block 679 from the software component illustrated in FIG. 14 when a deposit signal 525 has been received and a reasonable time has passed without the reception of a location signal 535. The term reasonable time is defined by a variable in software 600 varies for different applications. In an exemplary embodiment, the variable corresponding to a reasonable time is set at 1 second.

Software 600 at block 680 activates a default timer (not shown) which is in addition to the timers 561 discussed in relation to FIGS. 14 and 15. Software 600 records into memory 550 the compartment 570, 580, 590 into which waste 504 was deposited as represented by block 682. The software 600 further records into memory 550 the weight of waste 504, as represented by block 684. Software 600 determines if the default timer has expired at block 686. If the default timer has not expired, then software 600 awaits to include an additional deposit of waste 504 in waste disposal event 578, at decision block 688. When the default timer expires, software 600 determines if identification member 530 has received a valid identification signal 509 and has generated location signal 535, as illustrated by block 690. If location signal 535 has been generated, then waste disposal event 578 is attributable to the person 507 identified by location signal 535, and such information is stored within memory 550 as indicated by block 692. If a location signal 535 is not received, then waste disposal event 578 is marked as unassigned at block 694.

Waste segregation compliance system 500 allows healthcare facilities to determine caregiver compliance with waste disposal protocols by providing data which is presentable in various types of compliance reports. For example, a hospital summary report provides a summary of the waste disposal statistics and waste disposal costs for the hospital as a whole and specific departments within a healthcare environment. The purpose of the report is to identify departments within the hospital which have the most difficulty with waste segregation compliance so that corrective action may be taken. FIG. 18 shows an example of a department summary report 699. The department summary report 699 provides a summary of the waste disposal statistics and disposal costs for a specific department within a healthcare environment. The purpose of the report is to identify areas within the unit of caregivers which have the most difficulty with compliance so that corrective action may be taken.

As shown in FIG. 18, the department summary report 699 includes the department name 700, the time period for which the report is generated 701 and overall department waste statistics 702, 703 and 704. The report 699 further provides an overall department total disposal weight 705 and a department disposal cost 706. The report 699 also breaks the department into specific caregivers or groups 707. The report 699 provides waste statistics 708, 709 and 711, along with weight 713 and disposal costs 715 for each caregiver or group. This breakdown allows the person viewing the report to determine which employees or groups are having the most difficulty with waste segregation compliance. Departments can be charged for waste disposal or credited for recyclables as an additional incentive to segregate waste.

FIGS. 19A through 23B illustrate several different embodiments of a waste receptacle in accordance with the present invention. Each waste receptacle 710, 810, 910, 1010, and 1110 is interchangeable with waste receptacle 110, 210 and 512 as identified above. In one embodiment, each waste receptacle 710, 810, 910, 1010, and 1110 is similar to waste receptacle 110 and includes a detection member generally similar to detection member 120, an identification member generally similar to identification member 130, a reporting member generally similar to reporting member 140, a memory generally similar to memory 150, and a processor generally similar to processor 160. In another embodiment, each waste receptacle 710, 810, 910, 1010, and 1110 is similar to waste receptacle 210 and includes a detection member generally similar to detection member 220, an identification member generally similar to identification member 230, a reporting member generally similar to reporting member 240, a memory generally similar to memory 250, and a processor generally similar to processor 260. In yet another embodiment, each waste receptacle 710, 810, 910, 1010, and 1110 is similar to waste receptacle 512 and includes a detection member generally similar to detection member 520, an identification member generally similar to identification member 530, a reporting member generally similar to reporting member 540, a memory generally similar to memory 550, and a processor generally similar to processor 560.

Figure 19A:
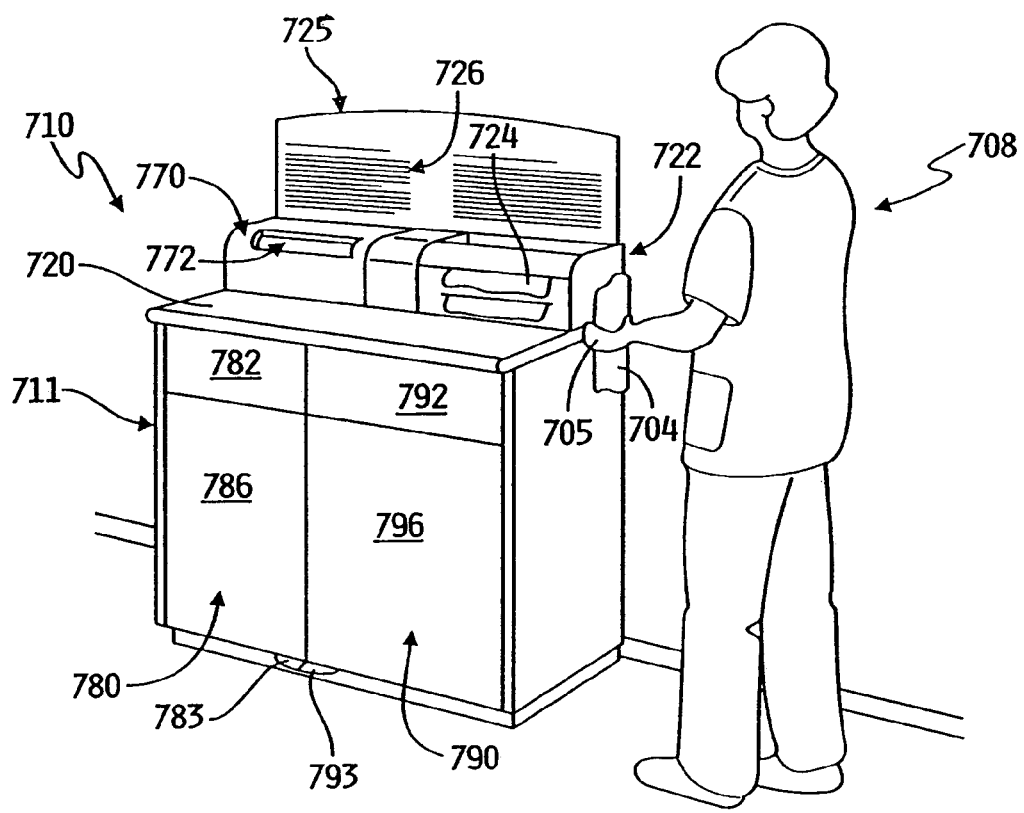
FIG. 19A is a perspective view of a second embodiment of the waste receptacle of the present invention for use by a caregiver.
Figure 19B:
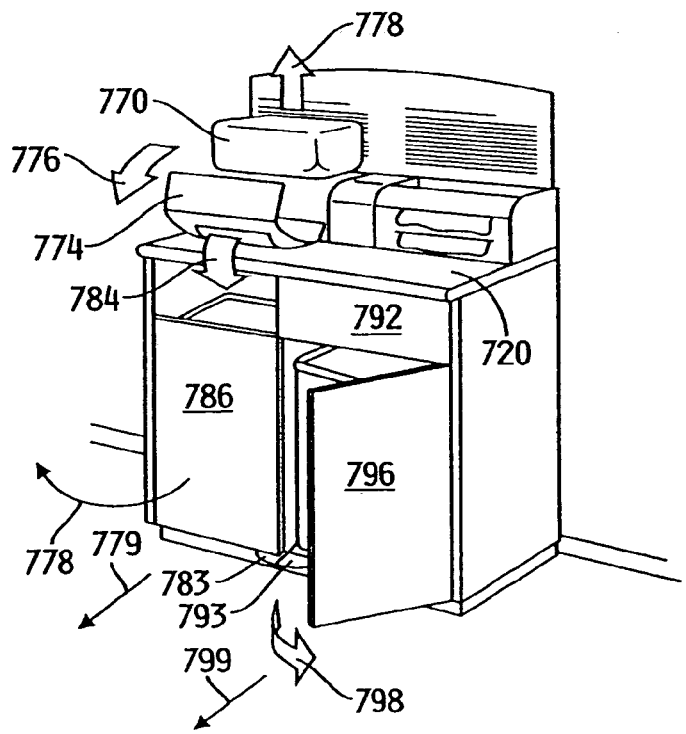
FIG. 19B is a perspective view of the waste receptacle of FIG. 19A, illustrating the operation of the waste receptacle.

Referring further to FIGS. 19A and 19B, waste receptacle 710 includes a housing 711, a first compartment 770, a second compartment 780, and a third compartment 790. Waste 704 is deposited by a person 708 into compartment 770 through an opening 772. Compartment 770 is removable from housing 711 by rotating cover 774 in a direction illustrated by arrow 776 in FIG. 19B and then lifting compartment 770 in a vertical direction illustrated by arrow 778 in FIG. 19B. Waste 704 is deposited by a person 708 into compartment 780 by moving a hinged cover 782 in the direction illustrated by arrow 784 in FIG. 19B. Cover 782 is moved through a conventional linkage (not shown) in response to person 708 stepping on foot pedal 783. Compartment 780 is removable from housing 711 by opening a hinged cover 786 in a direction indicated by arrow 778 in FIG. 19B and by moving compartment 780 in a direction illustrated by arrow 779 in FIG. 19B. Waste 704 is deposited by a person 708 into compartment 790 by moving a hinged cover 792 in the direction illustrated by arrow 784 in FIG. 19B. Cover 792 is moved through a conventional linkage (not shown) in response to person 708 stepping on foot pedal 793. Compartment 790 is removable from housing 711 by opening a hinged cover 796 in a direction indicated by arrow 798 in FIG. 19B and by moving compartment 790 in a direction illustrated by arrow 799 in FIG. 19B.

Waste receptacle 710 further includes a generally horizontal surface 720 which provides a work surface for person 708. Waste receptacle 710 additionally includes a dispenser 722. In one embodiment, dispenser 722 dispenses waste bags 724 to be used in connection with compartments 770, 780, and 790. In an alternative embodiment, dispenser 722 supplies wipes which are used by person 708 to sanitize their hands 705. Waste receptacle 710 further includes a panel 725. Panel 725 includes printed instructions 726 which detail the guidelines for proper waste disposal.

Figure 20A:
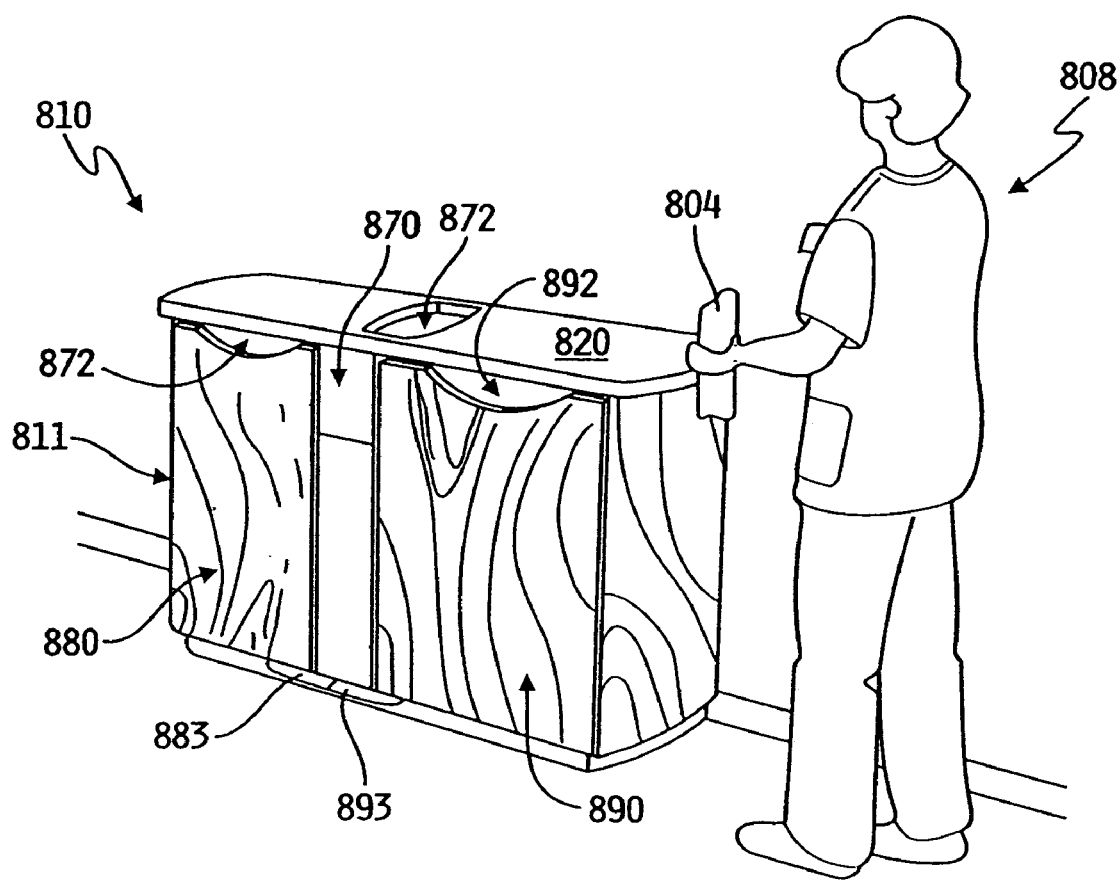
FIG. 20A is a perspective view of a third embodiment of the waste receptacle of the present invention for use by a caregiver.
Figure 20B:
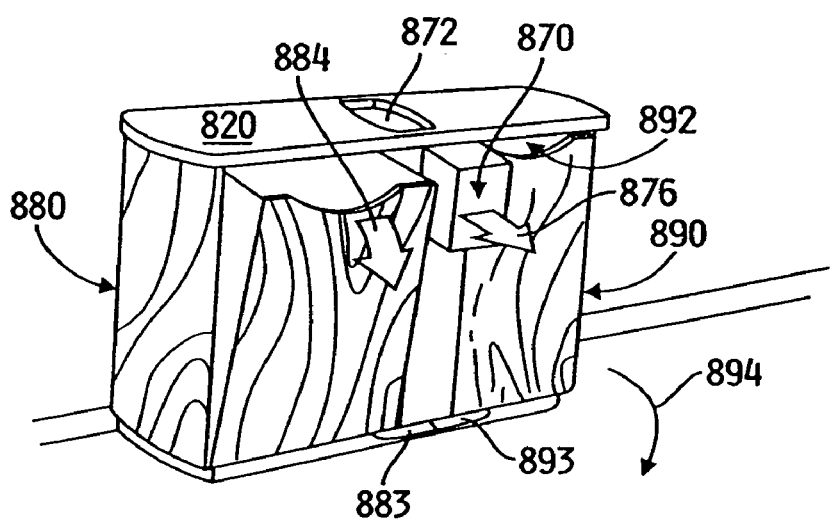
FIG. 20B is a perspective view of the waste receptacle of FIG. 20A, illustrating the operation of the waste receptacle.

Referring to FIGS. 20A and 20B, waste receptacle 810 includes a housing 811 having a generally horizontal surface 820 which provides a work surface for person 808, a first compartment 870, a second compartment 880, and a third compartment 890. Waste 804 is deposited by a person 808 into compartment 870 through an opening 872 formed within surface 820. Compartment 870 is removable from housing 811 by moving compartment 870 a direction illustrated by arrow 876 in FIG. 20B. Waste 804 is deposited by a person 808 into compartment 880 in one of two ways. Small items are deposited into compartment 880 directly through opening 872. Larger items are deposited in compartment 880 by tilting compartment 880 in a direction indicated by arrow 884 in FIG. 20B. Compartment 880 is tilted in response to person 808 stepping on foot pedal 883. Compartment 880 is removable from housing 811 to facilitate the emptying of waste 804 from compartment 880. Waste 804 is deposited by a person 808 into compartment 890 in one of two ways. Small items are deposited into compartment 890 directly through opening 892. Larger items are deposited in compartment 890 by tilting compartment 890 in a direction indicated by arrow 894 in FIG. 20B. Compartment 890 is tilted in response to person 808 stepping on foot pedal 893. Compartment 890 is removable from housing 811 to facilitate the emptying of waste 804 from compartment 890.

Figure 21A:
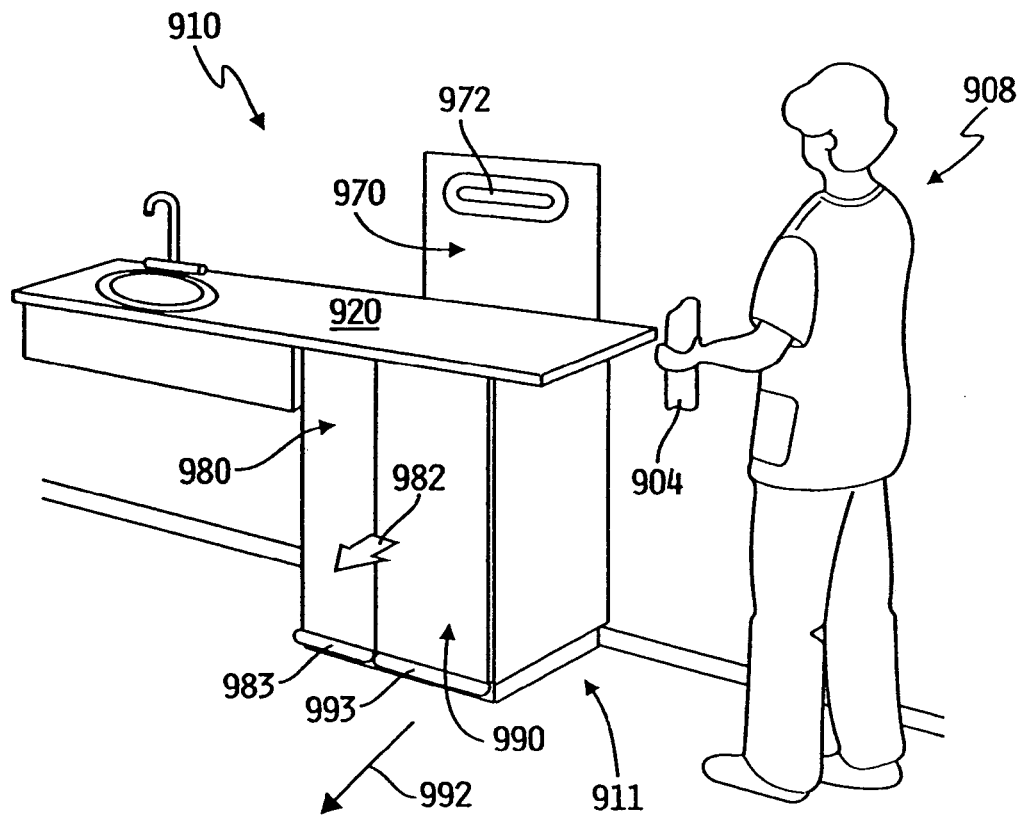
FIG. 21A is a perspective view of a fourth embodiment of the waste receptacle of the present invention for use by a caregiver.
Figure 21B:
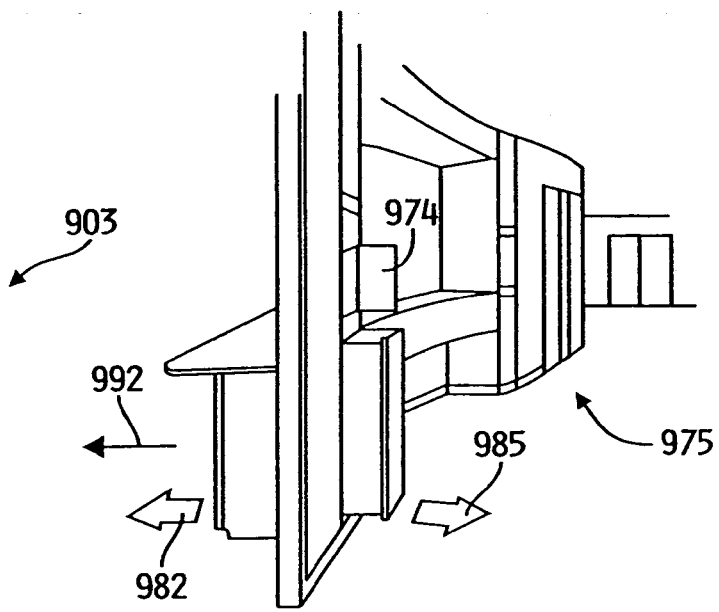
FIG. 21B is a perspective view of the waste receptacle of FIG. 21A, illustrating the operation of the waste receptacle.

Referring now to FIGS. 21A and 21B, waste receptacle 910 includes a housing 911 having a generally horizontal surface 920 which provides a work surface for person 908, a first compartment 970, a second compartment 980, and a third compartment 990. Waste 904 is deposited by a person 908 into compartment 970 through an opening 972. Compartment 970 is removable by opening a hinged door 974 located in a hallway 975 outside of patient room 903 as illustrated in FIG. 21B. Waste 904 is deposited by a person 908 into compartment 980 by moving compartment 980 in a direction indicated by arrow 982 in FIG. 21A and FIG. 21B. Compartment 980 is moved in response to person 908 stepping on foot pedal 983. Compartment 980 is removable from housing 911 to facilitate the emptying of waste 904 from compartment 980. Waste 904 is deposited by a person 908 into compartment 990 by moving compartment 990 in a direction indicated by arrow 992 in FIG. 21A and FIG. 21B. Compartment 990 is moved in response to person 908 stepping on foot pedal 993. Compartment 990 is removable from housing 911 to facilitate the emptying of waste 904 from compartment 990.

Compartments 980 and 990 are removable from housing 911 by moving the selected compartment in a direction indicated by arrow 985 in FIG. 21B. As shown in FIG. 21B, compartments 980 and 990 are emptied in hallway 975. By emptying each compartment 970, 980 and 990 in hallway 975 instead of in patient room 903, the risk of infection to the patient is reduced.

Figure 22A:
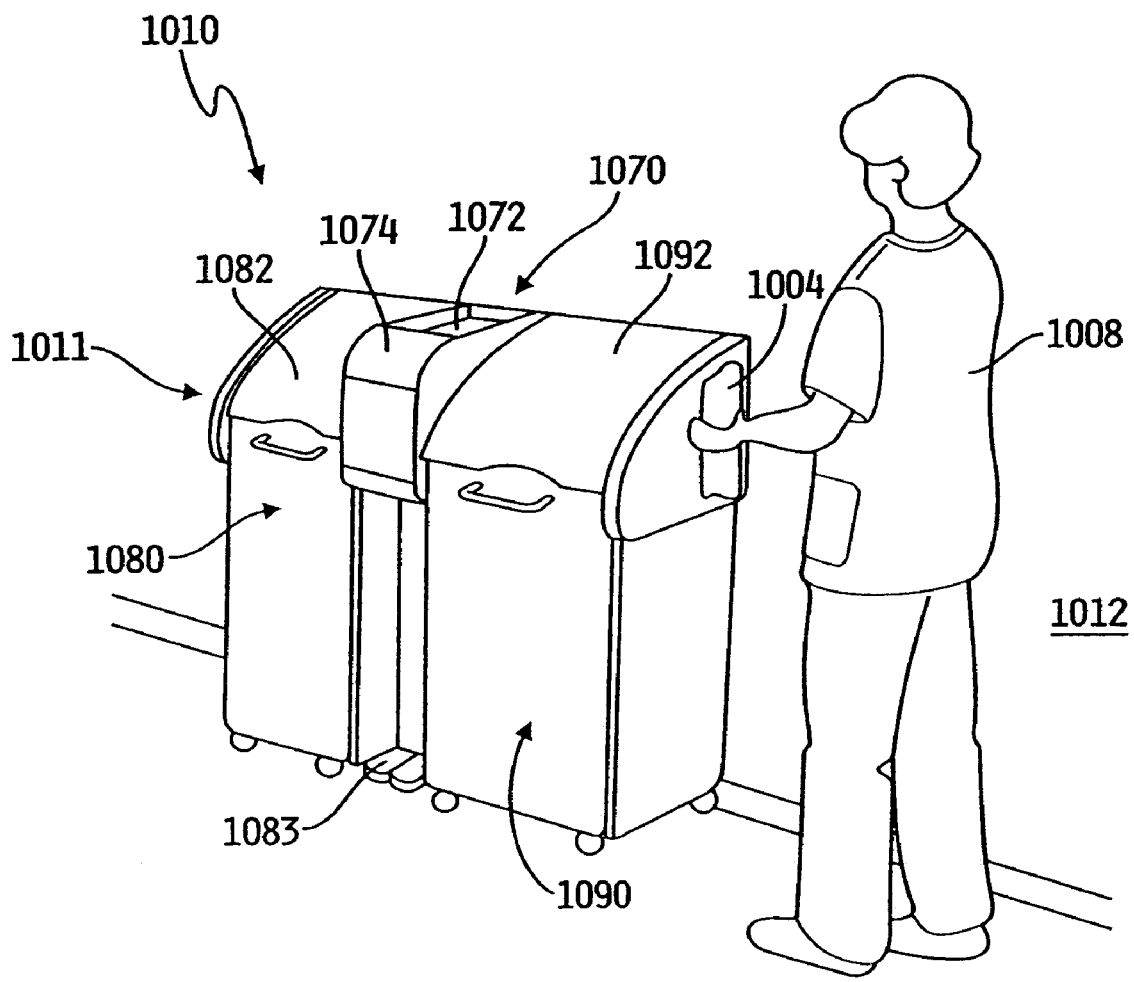
FIG. 22A is a perspective view of a fifth embodiment of the waste receptacle of the present invention for use by a caregiver.
Figure 22B:
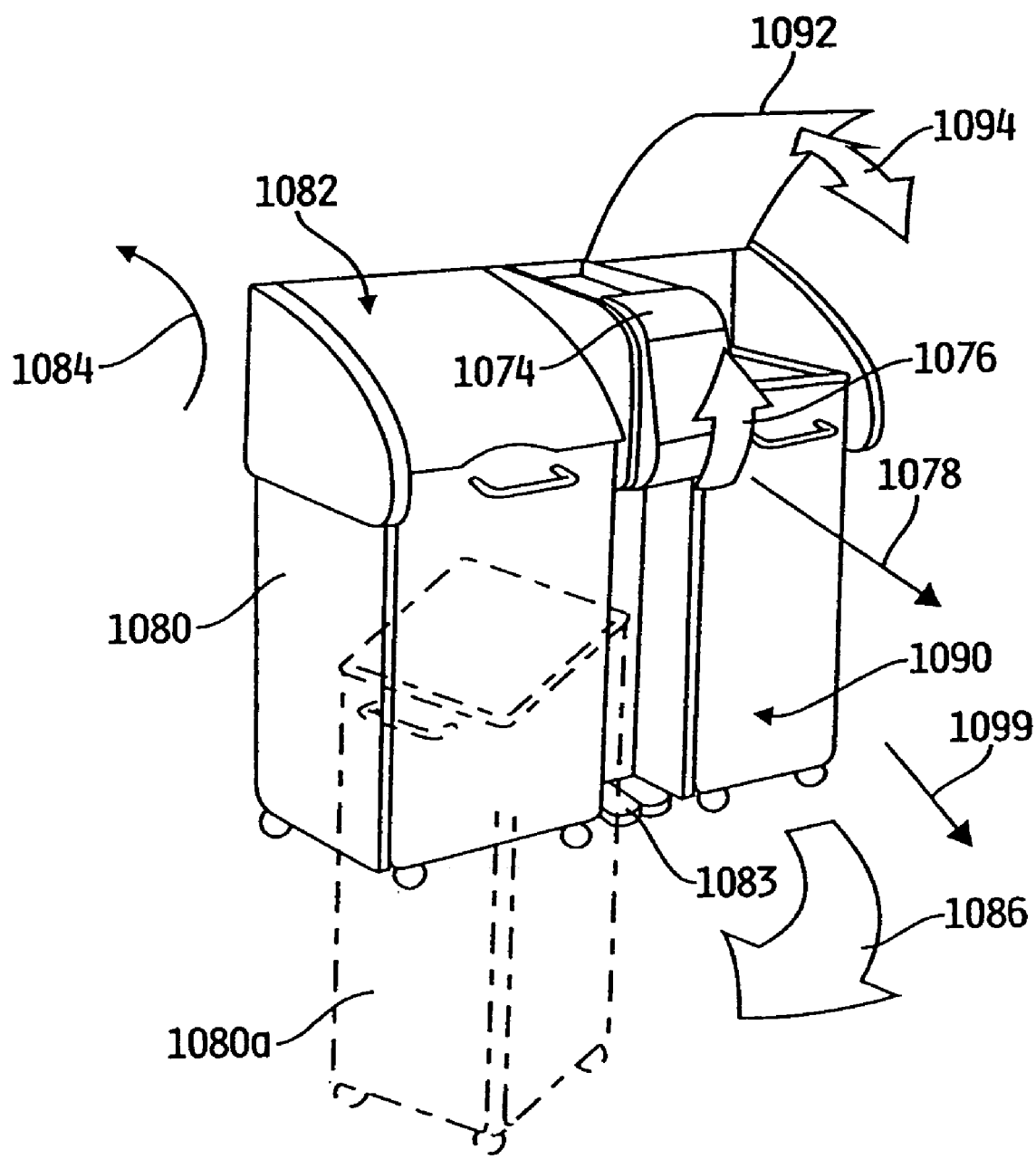
FIG. 22B is a perspective view of the waste receptacle of FIG. 22A, illustrating the operation of the waste receptacle.

Referring to FIGS. 22A and 22B, waste receptacle 1010 includes a housing 1011, a compartment 1070, a compartment 1080, and a compartment 1090. Housing 1011 is attached directly to a wall 1012. Waste 1004 is deposited by a person 1008 into compartment 1070 through an opening 1072. Compartment 1070 is removable from housing 1011 by rotating cover 1074 in a direction illustrated by arrow 1076 in FIG. 22B and then moving compartment 1070 in a direction illustrated by arrow 1078 in FIG. 22B. Waste 1004 is deposited by a person 1008 into compartment 1080 by moving a hinged cover 1082 in the direction illustrated by arrow 1084 in FIG. 22B. Cover 1082 is moved in response to person 1008 stepping on foot pedal 1083. Compartment 1080 is removable from housing 1011 by opening hinged cover 1082 and by moving compartment 1080 in a direction illustrated by arrow 1086 in FIG. 22B. Compartment 1080a is shown in FIG. 22B to illustrate compartment 1080 in a state of removal from housing 1011. Waste 1004 is deposited by a person 1008 into compartment 1090 by moving a hinged cover 1092 in the direction illustrated by arrow 1084 in FIG. 22B. Cover 1092 is moved in response to person 1008 stepping on foot pedal 1093. Compartment 1090 is removable from housing 1011 by opening hinged cover 1092 in a direction indicated by arrow 1094 and by moving compartment 1090 in a direction illustrated by arrow 1099 in FIG. 22B.

Figure 23A:
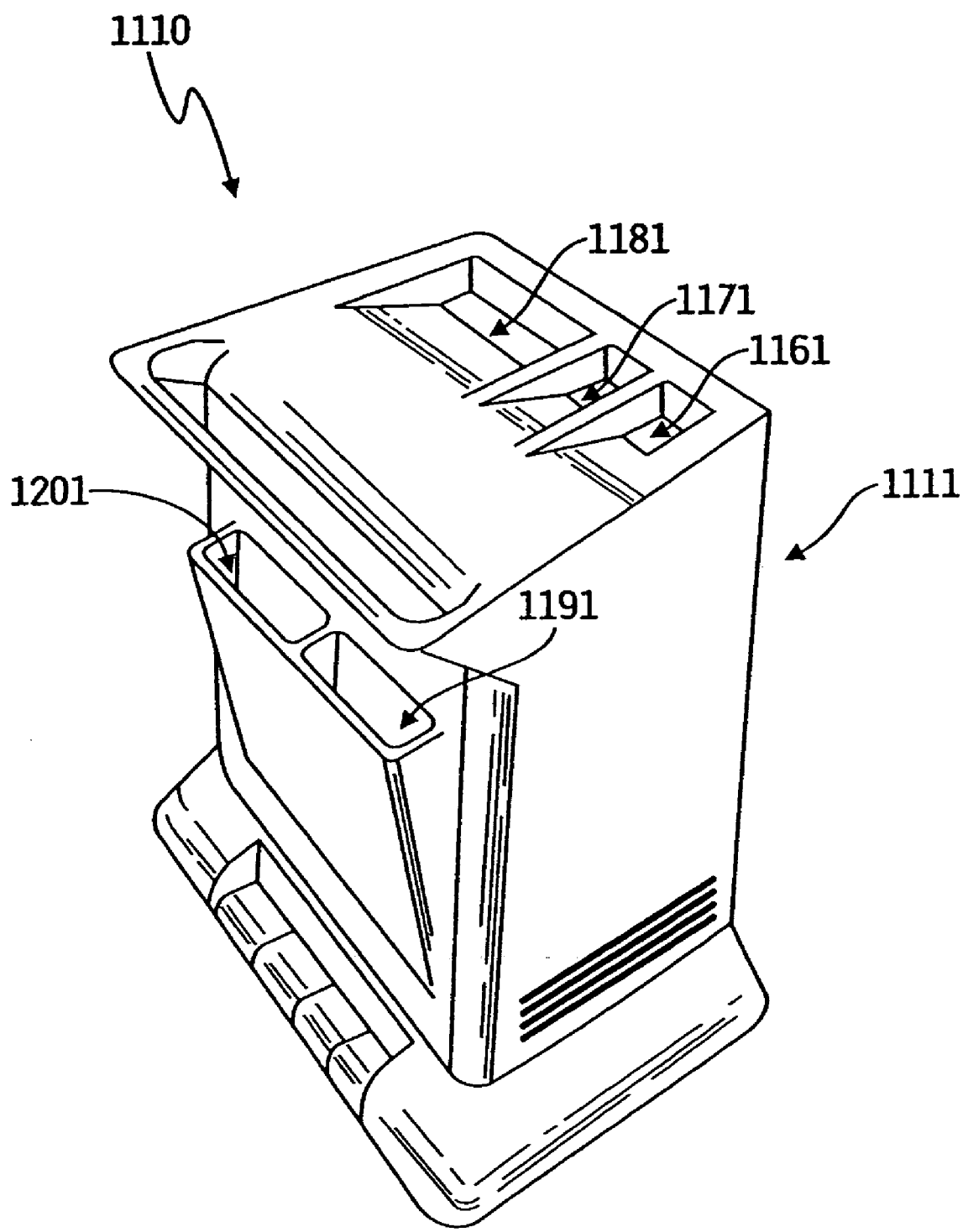
FIG. 23A is a front, perspective view of a sixth embodiment of the waste receptacle of the present invention.
Figure 23B:
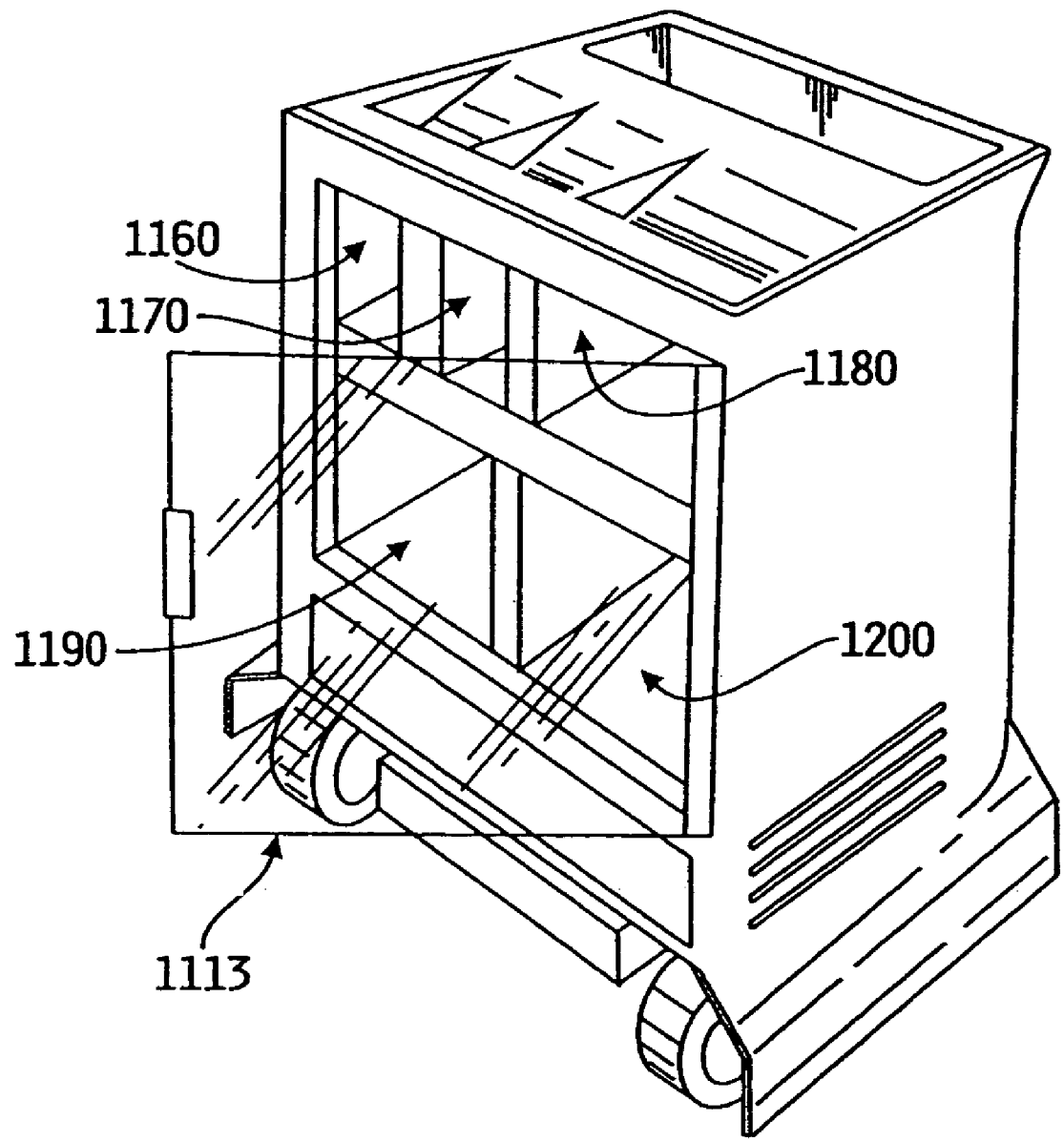
FIG. 23B is a rear, perspective view of the waste receptacle of FIG. 23A of the waste receptacle of the present invention.

Referring to FIGS. 23A and 23B, waste receptacle 1110 contains a housing 1111 and multiple waste compartments 1160, 1170, 1180, 1190, and 1200 to facilitate the effective segregation of waste 1104. Each compartment 1160, 1170, 1180, 1190, and 1200 includes a respective opening 1161, 1171, 1181, 1191, and 1201 to permit the placement of waste 1104 into each respective compartment 1160, 1170, 1180, 1190, and 1200 from the outside of waste receptacle 1110.

During proper use of waste receptacle 1110, person 1108 is to deposit waste 1104 into the compartment 1160, 1170, 1180, 1190, and 1200 which corresponds to the type of waste being disposed. Each compartment 1160, 1170, 1180, 1190, and 1200 is removable from housing 1111 by opening hinged cover 1113.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention are desired to be protected.

The invention claimed is:

1. A computer readable medium for use with a processor associated with a waste receptacle, the waste receptacle having a first detector configured to receive an identification signal from a transmitter associated with a person proximate to the waste receptacle and at least a first compartment with an associated first waste detector and a second compartment with an associated second waste detector, the computer readable medium comprising a plurality of instructions which when executed by the processor cause the processor to:

process information received by the first detector to determine the identity of the person;

process information received from the first waste detector and the second waste detector to determine if waste has been deposited in the respective first compartment and second compartment;

in response to a determination that waste has been deposited in the waste receptacle, associating the identified person with the deposited waste; and providing information representative of the identity of the person and into which of first compartment and second compartment waste was deposited to a remote computer.

2. The computer readable medium of claim 1, wherein the first compartment is associated with infectious medical waste and has a first associated disposal cost and the second compartment is associated with general waste and has a second associated disposal cost.

3. The computer readable medium of claim 2, wherein the instructions when executed by the processor further cause the processor to calculate a composite disposal cost associated with the waste deposited in the waste receptacle based on which compartments of the first compartment and the second compartment waste was deposited in and the first associated disposal cost and the second associated disposal cost.

4. The computer readable medium of claim 3, wherein at least a portion of the waste provides identification information to the first detector and the instructions when executed by the processor further cause the processor to determine the type of asset deposited in the waste receptacle.

5. The computer readable medium of claim 3, wherein the instructions when executed by the processor further cause the processor to provide the composite disposal cost to the remote computer.

6. The computer readable medium of claim 1, wherein the instructions when executed by the processor further cause the processor to calculate a composite cost associated with the waste deposited in the waste receptacle.

7. The computer readable medium of claim 1, wherein the instructions when executed by the processor further cause the processor to associate the deposited waste with the identified person if the relative time period between the waste being deposited and the person being identified is less than a threshold value.

8. The computer readable medium of claim 1, wherein the instructions when executed by the processor further cause the processor to continuously monitor the first detector for information to process.

9. The computer readable medium of claim 1, wherein the instructions when executed by the processor further cause the processor to monitor the first detector in response to processing information from one of the first waste detector and the second waste detector.

10. A computer readable medium for use with a processor associated with a waste segregation compliance system including at least a first waste receptacle positioned within a facility and having at least a first compartment and a second compartment and a locating and tracking system, the locating and tracking system including a plurality of transmitters associated with respective assets each transmitter configured to transmit an identification signal and a plurality of detectors positioned within the facility each detector configured to receive the identification signal from transmitters proximate to the detector, the computer readable medium comprising a plurality of instructions which when executed by the processor cause the processor to:

process information received by the plurality of detectors representative of the location of at least a first transmitter of the plurality of the transmitters;

track the location of the asset associated with the first transmitter as the asset moves throughout the facility based on the received information representative of the location of the first transmitter;

process information received from the first waste receptacle representative of the placement of waste in at least one of the first compartment and the second compartment;

associate the placement of waste in the waste receptacle with the first transmitter based on the proximity of the first transmitter to the waste receptacle at or near the time of the placement of waste in the waste receptacle; and provide information representative of the first transmitter associated with the placement of the waste in the waste receptacle and information representative of the amount of waste placed in each compartment of the waste receptacle.

11. The computer readable medium of claim 10, wherein the first compartment is associated with infectious medical waste and has a first associated disposal cost and the second compartment is associated with general waste and has a second associated disposal cost.

12. The computer readable medium of claim 11, wherein the instructions when executed by the processor further cause the processor to calculate a composite disposal cost associated with the waste deposited in the waste receptacle based on which compartments of the first compartment and the second compartment waste was deposited in and the first associated disposal cost and the second associated disposal cost.

13. The computer readable medium of claim 12, wherein the placement of waste in the waste receptacle is associated with the first transmitter if the relative time period between the waste being deposited and the detection of the first transmitter is less than a threshold value.

14. The computer readable medium of claim 10, wherein the first transmitter is associated with a person.

15. The computer readable medium of claim 10, wherein the first transmitter is associated with a disposable item.

16. The computer readable medium of claim 10, wherein a second transmitter is associated with a disposable item and a first detector is positioned at an entrance to the facility and wherein the instructions when executed by the processor further cause the processor to add the disposable item to an inventory when the disposable item enters the facility through the entrance.

17. The computer readable medium of claim 16, wherein when the disposable item associated with the second transmitter is placed in the waste receptacle the plurality of instructions cause the processor to remove the disposable item from the inventory.

18. A computer readable medium for use with a processor associated with a waste receptacle having at least a first compartment and a second compartment and a locating and tracking system, the locating and tracking system including a master station and plurality of detectors positioned throughout a facility, including a first detector associated with the waste receptacle, each of the detectors being configured to receive a respective identification signal from each of a plurality of transmitters, the computer readable medium comprising a plurality of instructions which when executed by the processor cause the processor to:

monitor at least the first detector to determine if a first transmitter of the plurality of transmitters is proximate to the associated waste receptacle;

monitor the first compartment of the waste receptacle and the second compartment of the waste receptacle to determine if waste has been deposited within one of the first compartment and the second compartment, a first determination being associated with the depositing of waste within one of the first compartment and the second compartment and a second determination being associated with the absence of the depositing of waste within one of the first compartment and the second compartment;

in response to a first determination that waste has been deposited within one of the first compartment and the second compartment, associating the first transmitter with the deposited waste;

providing to the master station, in response to the first determination, information representative of the location of the first transmitter and the associated deposited waste; and providing to the master station, in response to the second determination, information representative of the location of the first transmitter.

19. The computer readable medium of claim 18, wherein the first compartment is associated with infectious medical waste and has a first associated disposal cost and the second compartment is associated with general waste and has a second associated disposal cost.

20. The computer readable medium of claim 19, wherein the instructions when executed by the processor further cause the processor to calculate a composite disposal cost associated with the waste deposited in the waste receptacle based on which compartments of the first compartment and the second compartment waste was deposited in and the first associated disposal cost and the second associated disposal cost.

* * * * *